(12) United States Patent
Liau

(10) Patent No.: US 7,204,982 B2
(45) Date of Patent: Apr. 17, 2007

(54) COMPOSITIONS AND METHODS FOR TREATMENT AND DETECTION OF MULTIPLE CANCERS

(75) Inventor: Linda M. Liau, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 538 days.

(21) Appl. No.: 10/188,840

(22) Filed: Jul. 2, 2002

(65) Prior Publication Data

US 2004/0005642 A1    Jan. 8, 2004

(51) Int. Cl.
*A61K 39/395*    (2006.01)

(52) U.S. Cl. .............. 424/130.1; 424/155.1; 424/185.1; 514/44; 536/23.1; 536/24.3

(58) Field of Classification Search .......... 514/2, 514/21, 44; 530/388.85, 387.1; 435/69.1, 435/9.1, 6; 424/187.1, 130.1, 155.1, 185.1; 536/23.1, 24.3
See application file for complete search history.

(56) References Cited

U.S. PATENT DOCUMENTS 5,840,708 A * 11/1998 Weiss .................... 514/44
5,912,143 A * 6/1999 Bandman et al. .......... 435/69.1
2002/0147147 A1 10/2002 Molling et al.

FOREIGN PATENT DOCUMENTS

| EP | 1 074 617 A2 | 2/2001 |
| WO | WO 02/22660 A2 | 3/2002 |
| WO | WO 200222660 A2 * | 3/2002 |

OTHER PUBLICATIONS

Sherman, M.I. Annals of NY Acad. Sci., 1990,616:201-204.*
Holt, J.Mol Med Today, 1996, 2:184-185.*
Rojanasakul, Y. Advanced Drug Delivery Reviews, 1996,18:115-131.*
Branch, A.D.Tibs, Feb. 1998, 23: pp. 45-50.*
Hanash, S. Nature Reviews, Applied Proteomics, Mar. 2005, 9-14.*
Freshney, I., Culture of Animal Cells, A Manual of Basic Technique, Alan R. Liss, Inc., 1983, New York, p. 4.*
Hartwell et al., Science, 1997, 278:64-1068).*
Dermer, G., Bio/Technology, 1994, 12:320.*
Gura, T., Science, 1997, 278:1041-1042.*
Jain, R, K., Sci. Am., 1994, 271:58-65.*
Curti, B.D., Crit. Rev. in Oncology/Hematology, 1993, 14:29-39.*
Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Sambrook et al, eds, 1989, 2nd ed, Molecular Cloning, a laboratory manual, Cold Spring Harbor Laboratory Press, Cold Spring Harbor, p. 11.52.*
Wang et al (PNAS, 1995, 92:3318-3322).*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Montesano, R et al,1996, Intl J Cancer, 69(3): 225-235.*
Burmer, GC et al, 1991, Environmental Health perspectives, 93: 27-31.*
Busken, C et al, Digestive Disease Week Abstracts and Itinerary Planner, 2003, abstract No. 850.*
W.K. Cavenee, "Accumulation of Genetic Defects during Astrocytoma Progression," Cancer, 1992, 70(6): 1788-1793.
L.M. Liau et al., "Identification of a Human Glioma-associated Growth Factor Gene, *granulin*, Using Differential Immuno-absorption," Cancer Research, 2000, 60: 1353-1360.
L.M. Liau et al., "Microarrays and the Genetic Analysis of Brain Tumors," Current Genomics, 2002, 3(1): 33-41.
M. Nagane et al., "Advances in the Molecular Genetics of Gliomas," Current Opinion in Oncology, 1997, 9: 215-222.
L. Zhang et al., "Gene Expression Profiles in Normal and Cancer Cells," Science, 1997, 276: 1268-1272.
T.M. Strom et al., NCBI Accession No. AJ005896, 1998, 2pp.
A Schmitt et al., NCBI Accession No. AX011651, 2000, 1pp.
R. Strausberg, NCBI Accession No. BC021213, 2002, 2pp.
T. Isogai et al., NCBI Accession No. AK023433, 2002, 2pp.
W.B. Li et al., dbEST Id 7913479, NCBI Accession No. AL578513, 2001, 2pp.
W.B. Li et al., dbEST Id 7891055, NCBI Accession No. AL556099, 2001, 2pp.
W.B. Li et al., dbEST Id 7897665, NCBI Accession No. AL562709, 2001, 2pp.
K. Blechschmidt et al., NCBI Accession No. AF196779, 1999, 61pp.
R. Strausberg, dbEST Id 11609265, NCBI Accession No. BM925837, 2002, 2pp.
W.B. Li et al., dbEST Id 7890454, NCBI Accession No. AL555498, 2001, 2pp.
R. Strausberg, dbEST Id 9642741, NCBI Accession No. BI823463, 2001, 2pp.
R. Strausberg, dbEST Id 11116863, NCBI Accession No. BM544778, 2002, 2pp.
R. Strausberg, dbEST Id 8568806, NCBI Accession No. BG828872, 2001, 2pp.

(Continued)

*Primary Examiner*—Jeffrey Siew
*Assistant Examiner*—Minh-Tam Davis
(74) *Attorney, Agent, or Firm*—Canady + Lortz LLP; Karen S. Canady

(57) ABSTRACT

The invention provides a method for inhibiting proliferation of cancer cells, as well as methods for detecting and treating various cancers, including cancer of the brain, lung, breast, prostate and colon. The method comprises contacting a cancer cell with a molecule that disrupts the biological activity of a GDOX molecule. In one embodiment, the molecule is an antibody directed against a GDOX peptide. In other embodiments, the molecule is an antisense nucleotide directed against a GDOX nucleic acid molecule, or a vaccine comprising a GDOX peptide or a polynucleotide encoding a GDOX peptide. The invention additionally provides methods for detecting and treating cancer using GDOX-related molecules.

5 Claims, 9 Drawing Sheets

OTHER PUBLICATIONS

R. Strausberg, dbEST Id 11137339, NCBI Accession No. BM563934, 2002, 2pp.
R. Strausberg, dbEST Id 11120666, NCBI Accession No. BM548567, 2002, 2pp.
R. Strausberg, dbEST Id 6786993, NCBI Accession No. BF339883, 2000, 2pp.
R. Strausberg, dbEST Id 11124903, NCBI Accession No. BM 552522, 2002, 2pp.
R. Strausberg, dbEST Id 11363630, NCBI Accession No. BM801598, 2002, 2pp.
R. Strausberg, dbEST Id 7417187, NCBI Accession No. BF967572, 2001, 2pp.
W.B. Li et al., dbEST Id 7912948, NCBI Accession No. AL577982, 2001, 2pp.
R. Strausberg, dbEST Id 6961642, NCBI Accession No. BF525597, 2000, 2pp.
R. Strausberg, dbEST Id 9823795, NCBI Accession No. BI914036, 2001, 2pp.
R. Strausberg, dbEST Id 8519963, NCBI Accession No. BG759829, 2001, 2pp.
R. Strausberg, dbEST Id 9641131, NCBI Accession No. BI821858, 2001, 2pp.
R. Strausberg, dbEST Id 7128546, NCBI Accession No. BF663215, 2000, 2pp.
R. Strausberg, dbEST Id 9817876, NCBI Accession No. BI908155, 2001, 2pp.
R. Strausberg, dbEST Id 6682186, NCBI Accession No. BF237784, 2000, 2pp.
R. Strausberg, dbEST Id 9643781, NCBI Accession No. BI824500, 2001, 2pp.
R. Strausberg, dbEST Id 7418555, NCBI Accession No. BF968709, 2001, 2pp.
R. Strausberg, dbEST Id 9826444, NCBI Accession No. BI916663, 2001, 2pp.
R. Strausberg, dbEST Id 7537145, NCBI Accession No. BF 980663, 2001, 2pp.
T. Ota et al., dbEST Id 6563809, NCBI Accession No. AU134850, 2000, 2pp.
R. Strausberg, dbEST Id 9824007, NCBI Accession No. BI914246, 2001, 2pp.
R. Strausberg, dbEST Id 6038328, NCBI Accession No. BE784473, 2000, 2pp.
R. Strausberg, dbEST Id 9608861, NCBI Accession No. BI767996, 2001, 2pp.
R. Strausberg, dbEST Id 9414614, NCBI Accession No. BI600570, 2001, 2pp.
R. Strausberg, dbEST Id 8963557, NCBI Accession no. BI199514, 2001, 2pp.
R. Strausberg, dbEST Id 5033672, NCBI Accession No. BE263463, 2000, 2pp.
R. Strausberg, dbEST Id 5686922, NCBI Accession No. BE514230, 2000, 2pp.
M.F. Bonaldo et al., dbEST Id 11633144, NCBI Accession No. BM931103, 2002, 2pp.
M.F. Bonaldo et al., dbEST Id 11301541, NCBI Accession No. BM720608, 2002, 2pp.
R. Strausberg, dbEST Id 8480717, NCBI Accession No. BG720198, 2001, 2pp.
R. Strausberg, dbEST Id 7417116, NCBI Accession No. BF967514, 2001, 2pp.
R. Strausberg, dbEST Id 5020715, NCBI Accession No. BE254555, 2000, 2pp.
Database Genbank, Accession No. ABB97608, Tang et al. Gene Sequence, Mar. 21, 2002. SEQ ID No. 876. MPSRCH search report, 2004, pct-us03-21013-2.rag, p. 2

* cited by examiner

Fig. 1A

```
                              M   S   E   V   R   L   P   P   L   R   A   L   D   D   F
  1    CACATTAACC GGCAGGATGT CGGAGGTGCG GCTGCCACCG CTACGCGCCC TGGACGACTT
       V   L   G │ S   A   R │ L   A   A   P   D   P   C   D   P   Q   R   W   C   H
 61    TGTTCTGGG  TCGGCGC   TC TGGCGGCTC CGGATCCATG CGACCCGCAG CGATGGTGCCA
       R   V   I   N   N   L   L   Y   Y   Q   T   N   Y   L   L   C   F   G   I   G
121    CCGCGTCATC AACAACCTCC TCTACTACCA AACCAACTAC CTTCTCTGCT TCGGCATCGG
       L   A   L   A   G   Y   V   R   P   L   H   T   L   L   S   A   L   V   V   A
181    CCTCGCTCTC GCCGGGTACG TGCGGCCACT TCATACGCTC CTGAGCGCGC TGGTAGTGGC
       V   A   L   G   V   L   V   W   A   A   E   T   R   A   A   V   R   R   C   R
241    GGTGGCCCTC GGCGTGCTGG TGTGGGCAGC TGAGACCCGC GCAGCTGTGC GCGCTGCCG
       R   S   H   P   A   A   C   L   A   A   V   L   A   V   G   L   L   V   L   W
301    CCGCAGCCAC CCTGCAGCCT GCCTGGCCGC AGTGCTTGCC GTCGGCCTCC TGGTGCTCTG
       V   A   G   G   A   C   F   L   F   S   I   A   G   P   V   L   L   I   L
361    GGTCGCGGGC CGCGGCTGCA CCTTCCTGTT CAGCATCGCC GCGCCCGGTGC TTCTGATCCT
       V   H   A │ S   L   R │ L   R   N   L   K   N   K   I   E   N   K   I   E   S
421    GGTGCACGC  TCGTTGC   CCTGCGCAAC CTAAGAACAAG ATTGAGAACA AGATCGAGAG
       I   G   L   K   R   T   P   M   G   L   L   E   A   L   G   Q   E   Q   E
481    CATTGGTCTC AACCGGACGC CAATGGGCCT GCTACTAGAG GCACTGGGAC AAGAGCAGGA
       A   G   S
541    GGCTGGATCCTAGGCCCCTG GGATCTGTAC CCAGGACCTG GAGAATACCA CCCGACCCCC
601    AGCCCATAAT TGGGACCCAG AGCCCTTTCC CAGCACTTAA AACAGGAGCC TAGAGCCCCC
661    TGCCCAAACA AAACAGGACA TCTGTGACCG CCCTACCCCC ACGCCAGCCC CAAACTAAGA
721    TATCCCTCAC ACCCAGCCCC CATTACCTAG GACAAGAGT CTTCCCCAGC CTGAACCTA
781    GGACCAAGAG CCACCTACAT CCAGCCCCAA AACTGGGGCT TCAGGCCAGA GCATCCATGG
841    CCAATTTCAA ATTGTGAACC CAGAGACACT CCCATCCACC CTTCTCCATG CTCATCCCCA
901    AACTGGGGCC TGGAGCAAGG CACTCTCAAA TCTTGAACCC TGGACCAAAG CTTTTCCAGA
961    CCCCACCCTA CCTTCCAACC CAGGTCAAGA CATTGCCAAATCTTGAACTC AGAACCCAAG
1021   TGTTCCATGC CCCTGTGTGG ATGGAGTCGG GTATCCTGAC TGTTGGACCC CCTGGTCCAGG
1081   TGATCCCGAC CCTCACCAGT CCCATTTGCC CTCCCCCAGC TCTGCTTAGG CATTTGCCC
1141   CTCACCCCAA TGTTCCACAC CATCGACAAC CAAGGGGTGA GGTGCGGACA GGCCTCAGCA
1201   GGGAATGGGG CGTATATGTT AGTGTTGCTG CAACAATAAA GCCTGTTGCA TCTCTCATGC
1261   CAAAAAAAAAA AAAAAACGGCCGGCCGCTCTAGAGG
```

Fig. 3A-B
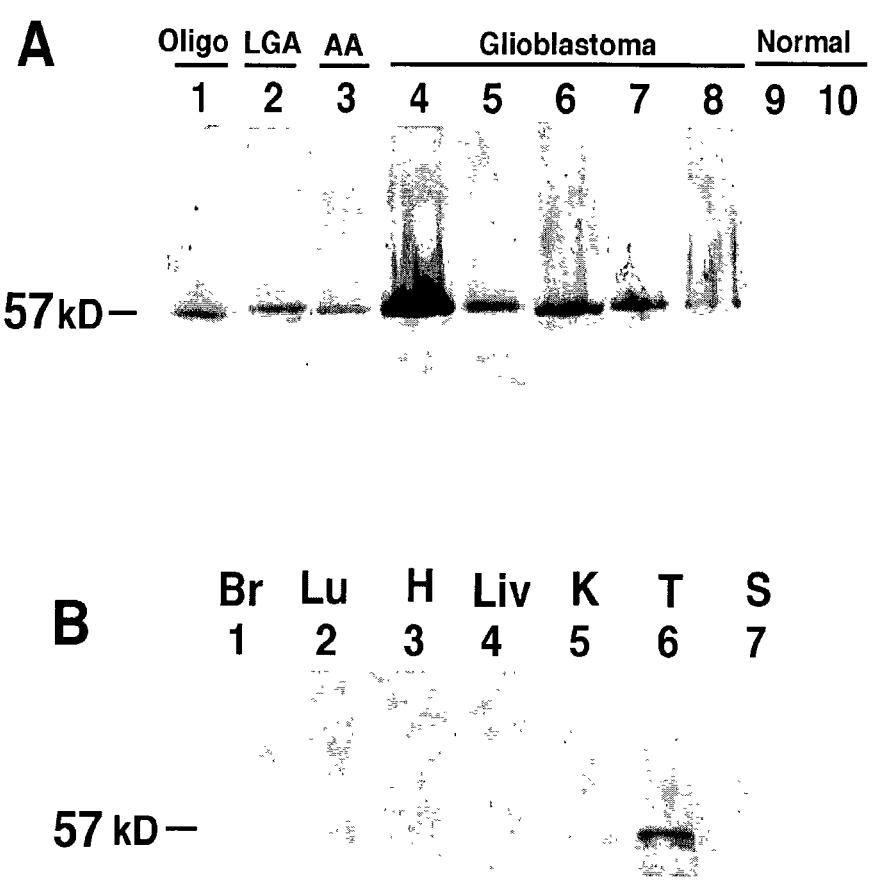

Fig. 7
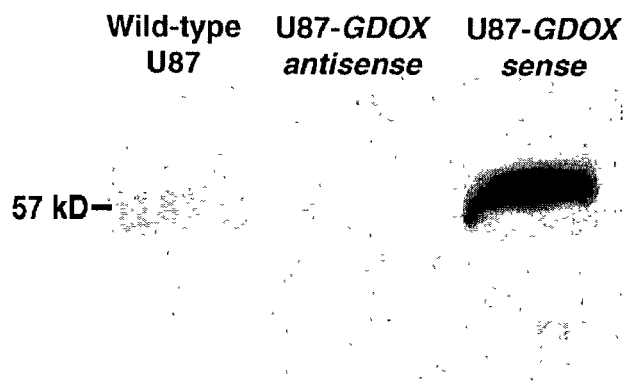
Fig. 8
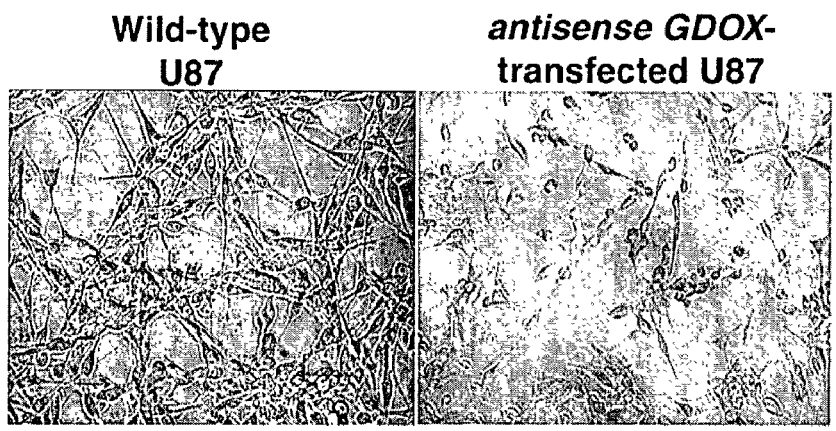
Fig. 9A     Fig. 9B

Fig. 12A
Brain Cancer
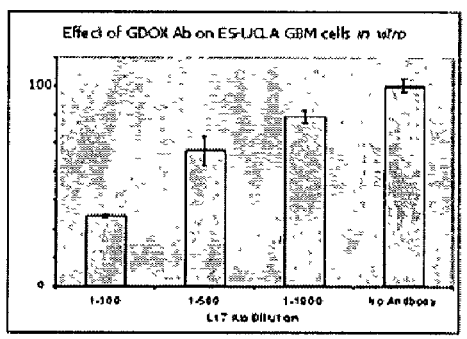
Fig. 12B
Breast Cancer
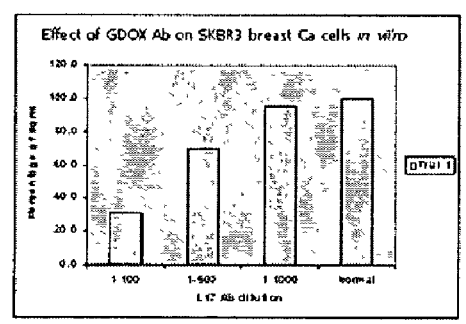
Lung Cancer
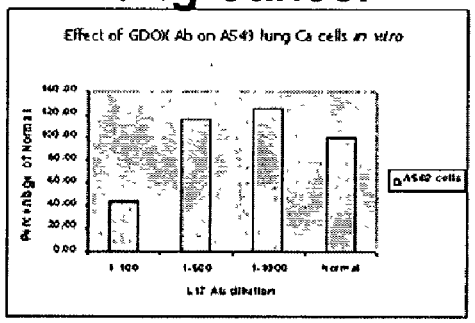
Prostate Cancer
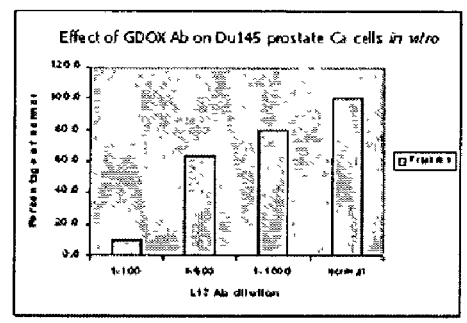
Fig. 12C
Fig. 12D

SEQUENCE LISTING

```
<160> NUMBER OF SEQ ID NOS: 4

<210> SEQ ID NO 1
<211> LENGTH: 1263
<212> TYPE: DNA
<213> ORGANISM: Homo sapiens

<400> SEQUENCE: 1
cacattaacc ggcaggatgt cggaggtgcg gctgccaccg ctacgcgccc tggacgactt      60
tgttctgggg tcggcgcgtc tggcggctcc ggatccatgc gacccgcagc gatggtgcca     120
ccgcgtcatc aacaacctcc tctactacca aaccaactac cttctctgct tcggcatcgg     180
cctcgctctc gccgggtacg tgcggccact tcatacgctc ctgagcgcgc tggtagtggc     240
ggtggccctc ggcgtgctgg tgtgggcagc tgagacccgc gcagctgtgc gccgctgccg     300
ccgcagccac cctgcagcct gcctggccgc agtgcttgcc gtcggcctcc tggtgctctg     360
ggtcgcgggc ggcgcttgca ccttcctgtt cagcatcgcc gggccggtgc ttctgatcct     420
ggtgcacgcc tcgttgcgcc tgcgcaacct taagaacaag attgagaaca agatcgagag     480
cattggtctc aagcggacgc caatgggcct gctactagag gcactgggac aagagcagga     540
ggctggatcc taggcccctg ggatctgtac ccaggacctg gagaatacca ccccacccc      600
```

```
                                                          -continued
agcccataat tgggacccag agcccttcc cagcacttaa aacaggagcc tagagccccc      660
tgcccaaaca aaacaggaca tctgtgaccg ccctacccccc acgccagccc caaactaaga    720
tatccctcac acccagcccc cattacctag ggacaagagt cttccccagc cttgaaccta    780
ggaccaagag ccacctacat ccagcccaa aactggggct tcaggccaga gcatccatgg     840
ccaatttcaa attgtgaacc cagagacact cccatccacc cttctccatg ctcatcccca    900
aactggggcc tggagcaagg cactctcaaa tcttgaaccc tggaccaaag cttttccaga    960
ccccacccta ccttccaacc caggtcaaga cattgccaaa tcttgaactc agaacccaag   1020
tgttccatgc ccctgtgtgg atggagtcgg gtatcctgac tgttggaccc ctggtccagg   1080
tgatcccgac cctcaccagt cccatttgcc tccctccagc tctgcttagg cattttgccc    1140
ctcaccccaa tgttccacac catcgacaac caagggtgac ggtggggaca ggcctcagca   1200
gggaatgggg cgtatatgtt agtgttgctg caacaataaa gcctgttgca tctctcatgc   1260
caa                                                                 1263

<210> SEQ ID NO 2
<211> LENGTH: 178
<212> TYPE: PRT
<213> ORGANISM: Homo sapiens

<400> SEQUENCE: 2

Met Ser Glu Val Arg Leu Pro Pro Leu Arg Ala Leu Asp Asp Phe Val
 1               5                  10                  15

Leu Gly Ser Ala Arg Leu Ala Ala Pro Asp Pro Cys Asp Pro Gln Arg
            20                  25                  30

Trp Cys His Arg Val Ile Asn Asn Leu Leu Tyr Tyr Gln Thr Asn Tyr
        35                  40                  45

Leu Leu Cys Phe Gly Ile Gly Leu Ala Leu Ala Gly Tyr Val Arg Pro
    50                  55                  60

Leu His Thr Leu Leu Ser Ala Leu Val Val Ala Val Ala Leu Gly Val
65                  70                  75                  80

Leu Val Trp Ala Ala Glu Thr Arg Ala Ala Val Arg Arg Cys Arg Arg
                85                  90                  95

Ser His Pro Ala Ala Cys Leu Ala Ala Val Leu Ala Val Gly Leu Leu
            100                 105                 110

Val Leu Trp Val Ala Gly Gly Ala Cys Thr Phe Leu Phe Ser Ile Ala
        115                 120                 125

Gly Pro Val Leu Leu Ile Leu Val His Ala Ser Leu Arg Leu Arg Asn
    130                 135                 140

Leu Lys Asn Lys Ile Glu Asn Lys Ile Glu Ser Ile Gly Leu Lys Arg
145                 150                 155                 160

Thr Pro Met Gly Leu Leu Leu Glu Ala Leu Gly Gln Glu Gln Glu Ala
                165                 170                 175

Gly Ser

<210> SEQ ID NO 3
<211> LENGTH: 19
<212> TYPE: PRT
<213> ORGANISM: Homo sapiens

<400> SEQUENCE: 3

His Ala Ser Leu Arg Leu Arg Asn Leu Lys Asn Lys Ile Glu Asn Lys
 1               5                  10                  15

Ile Glu Ser
```

```
<210> SEQ ID NO 4
<211> LENGTH: 20
<212> TYPE: PRT
<213> ORGANISM: Homo sapiens

<400> SEQUENCE: 4

Lys Arg Thr Pro Met Gly Leu Leu Leu Glu Ala Leu Gly Gln Glu Gln
 1               5                  10                  15

Glu Ala Gly Ser
            20
```

COMPOSITIONS AND METHODS FOR TREATMENT AND DETECTION OF MULTIPLE CANCERS

Throughout this application various publications are referenced. The disclosures of these publications in their entireties are hereby incorporated by reference into this application in order to describe more fully the state of the art to which this invention pertains.

TECHNICAL FIELD OF THE INVENTION

The present invention relates generally to detection and therapy of cancer. The invention is more specifically related to a novel gene, GDOX, and to GDOX-related molecules as therapeutic and diagnostic targets. GDOX antibodies and antisense nucleotides can be used in vaccines and pharmaceutical compositions for the treatment of various cancers expressing GDOX, as well as in methods of detecting and assessing the malignancy of such cancers. The invention further provides methods for identifying molecules useful in the treatment and detection of cancer.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

Cancer is the result of cumulative multiple genetic mutations, which result in the activation of oncogenes and/or the inactivation of tumor suppressor genes. It is the differential expression of these critical genes and their downstream effectors that enables cells to override growth controls and undergo carcinogenesis. The pathological changes that arise in cancer, whether caused by a single gene mutation or multiple genetic alterations, are essentially driven by changes in gene expression. In the malignant progression of astrocytic cancers, it has been shown that accumulation of multiple genetic lesions underlies the neoplastic process. These lesions include mutations of the genes p53, p16, RB, and PTEN, as well as amplification of CDK4 and EGFR (Furnari, F. et al., Cancer Surv., 25: 233–275, 1995; Cavenee, W., Cancer., 70: 1788–93, 1992). Although these known genetic abnormalities have been well-documented in the formation of the most malignant brain tumor, glioblastoma, recent insight into the extent of gene expression differences underlying malignancy reveals that hundreds of gene transcripts may be expressed at significantly different levels between normal and neoplastic cells (Zhang, L. et al., Science., 276: 1268–72, 1997). Therefore, there is considerable need for the identification of novel genes that are differentially expressed in brain and other cancer cells to further the understanding of the complex molecular basis of these cancers. Furthermore, this endeavor has direct clinical relevance when combined with therapies that specifically target these differentially expressed gene products.

A variety of methods are currently employed to isolate genes associated with particular differential phenotypes. Subtractive hybridization, differential display (DD), representational difference analysis (RDA), serial analysis of gene expression (SAGE), and suppression subtractive hybridization (SSH) all allow for the cloning and identification of differentially expressed sequences. While all these techniques identify tissue-enriched mRNAs, none select for tissue-specific proteins. There remains a need for molecules identified by a differential screening technique that provides actual confirmation of the presence of a protein product, not just the capacity to synthesize a protein. In addition, there is a need for tumor-associated proteins with antigenic determinants recognized by the immune system and capable of eliciting an effective immune response.

SUMMARY OF THE INVENTION

The invention meets these needs and others by providing compositions and methods for the treatment and detection of multiple cancers. More specifically, the invention provides GDOX related molecules, compositions and kits comprising GDOX related molecules, and methods of using GDOX related molecules for the treatment and detection of cancer. In one embodiment, the invention provides an expression vector comprising a nucleic acid molecule that encodes a GDOX protein operably linked to an expression control sequence. The nucleic acid molecule may encode the GDOX protein in a sense or anti-sense orientation, depending on the intended use. Also provided are host cells containing such expression vectors, which can be used for the production of GDOX related molecules. In some embodiments, the nucleic acid molecule is labeled with a detectable marker, or provided in a composition with a pharmaceutically acceptable carrier.

The invention additionally provides GDOX polypeptides, including immunogenic GDOX peptides comprising amino acids 62–65, 129–178, 137–155 and/or 159–178 of SEQ ID NO: 2. The GDOX polypeptide may be provided in a variety of forms, as appropriate for a particular use, including, for example, in a soluble form, immobilized on a substrate, or in combination with a pharmaceutically acceptable carrier. Antibodies directed against such GDOX polypeptides are also provided. In some embodiments, the antibody is labeled with a detectable marker, or provided in a composition with a pharmaceutically acceptable carrier.

The methods provided by the invention include a method for inhibiting proliferation of cancer cells comprising contacting a cancer cell with a molecule that disrupts the biological activity of a GDOX molecule. Typically, the biological activity comprises specific binding of GDOX to a GDOX antibody or expression of a GDOX polynucleotide. Other methods provided include a method for treating cancer in a subject by administering to the subject a molecule that disrupts the biological activity of a GDOX molecule, a method for detecting cancer, and a method for identifying a cancer that is sensitive to estrogen antagonists. The method for detecting cancer comprises contacting a tissue specimen with a detectable molecule that specifically binds a GDOX molecule and detecting binding of the detectable molecule. Binding of the detectable molecule is indicative of cancer. The method for identifying a cancer that is sensitive to estrogen antagonists comprises contacting a cancer specimen with a detectable molecule that specifically binds a GDOX molecule and detecting binding of the detectable molecule. Binding of the detectable molecule is indicative of cancer that is sensitive to estrogen antagonists. Examples of a detectable molecule include an antibody directed against a GDOX protein or an antisense nucleotide that specifically hybridizes to a GDOX nucleic acid molecule. Typically, the cancer cell is derived from brain, lung, prostate, colon or breast, or any other cancer associated with the overexpression of GDOX. Examples of brain cancer cells include glioblastoma, astrocytoma or oligodendroglioma cells. A representative estrogen antagonist is tamoxifen.

BRIEF DESCRIPTION OF THE FIGURES

FIG. 1A shows the nucleotide (SEQ ID NO: 1) and deduced amino acid (SEQ ID NO: 2) sequence of GDOX. The underlined region indicates the predicted GDOX open reading frame (ORF) with the corresponding amino acid sequence. The initiator codon (ATG) starts at nucleotide 17, and the stop codon (TAG) ends at 553. Predicted protein kinase C (PKC) phosphorylation sites (19–21 and 139–141) are boxed, and possible N-myristoylation sites (53–58 and 118–123) are indicated by dotted boxes.

FIG. 3A displays results of a western blot analysis of expression of GDOX protein in normal and tumorigenic brain tissues. Lanes 9 and 10 were non-tumorigenic brain tissues taken from a surgical decompression for trauma (lane 9) and autopsy normal brain specimen (lane 10). Lanes 1 thru 8 were surgically resected brain tumor tissues that were pathologically confirmed to be oligodendrogliomas (lane 1), low-grade astrocytoma (lane 2), anaplastic astrocytoma (lane 3), or glioblastoma (lanes 5–8).

FIG. 3B displays results of a western blot analysis of expression of GDOX protein in various human peripheral organs. Tissue specimens were taken at autopsy from normal brain (lane 1), lung (lane 2), heart (lane 3), liver (lane 4), kidney (lane 5), testes (lane 6), and spleen (lane 7). A predominant 57-kd protein was detected, along with a lighter 19-kd band. These proteins localized to the same tissue distribution as seen for GDOX mRNA by northern blot analysis.

FIG. 7 displays the results of Southern blotting of GDOX cDNA to human chromosomal DNA in somatic cell hybrid panel. DNA hybridization revealed a band of predicted size with human genomic DNA and with DNA from the somatic cell hybrid NA10324, which was the only hybrid represented in this mapping panel (Coriell Cell Repositories) that contained the human X chromosome. Therefore, the GDOX gene appears to be on human chromosome X.

FIG. 8 displays results of a western blot analysis to confirm presence and absence of expression of GDOX in human glioblastoma cells (U87 cell line) transfected with sense and antisense GDOX cDNA.

FIGS. 9A–B are phase contrast photomicrographs showing morphological changes in U87 cells transfected with antisense GDOX cDNA. The wild-type control U87 cells were highly reftractile and grew in large patches with cytoplasmic processes (FIG. 9A). The antisense GDOX-transfected cells did not grow well and had a more rounded morphology (FIG. 9B).

FIGS. 12A–D are bar graphs showing the growth suppressive effect of a specific anti-GDOX antibody in human tumor cell lines: FIG. 12A, ES-UCLA (primary glioblastoma); FIG. 12B, SKBR3 (breast adenocarcinoma); FIG. 12C, A549 (lung carcinoma); and FIG. 12D, Du145 (prostate cancer). Results were normalized in terms of percentage of control proliferation, with the control cells receiving equal volumes of heat-inactivated anti-GDOX antibody or a control antibody.

DETAILED DESCRIPTION OF THE INVENTION

Figure 1B:
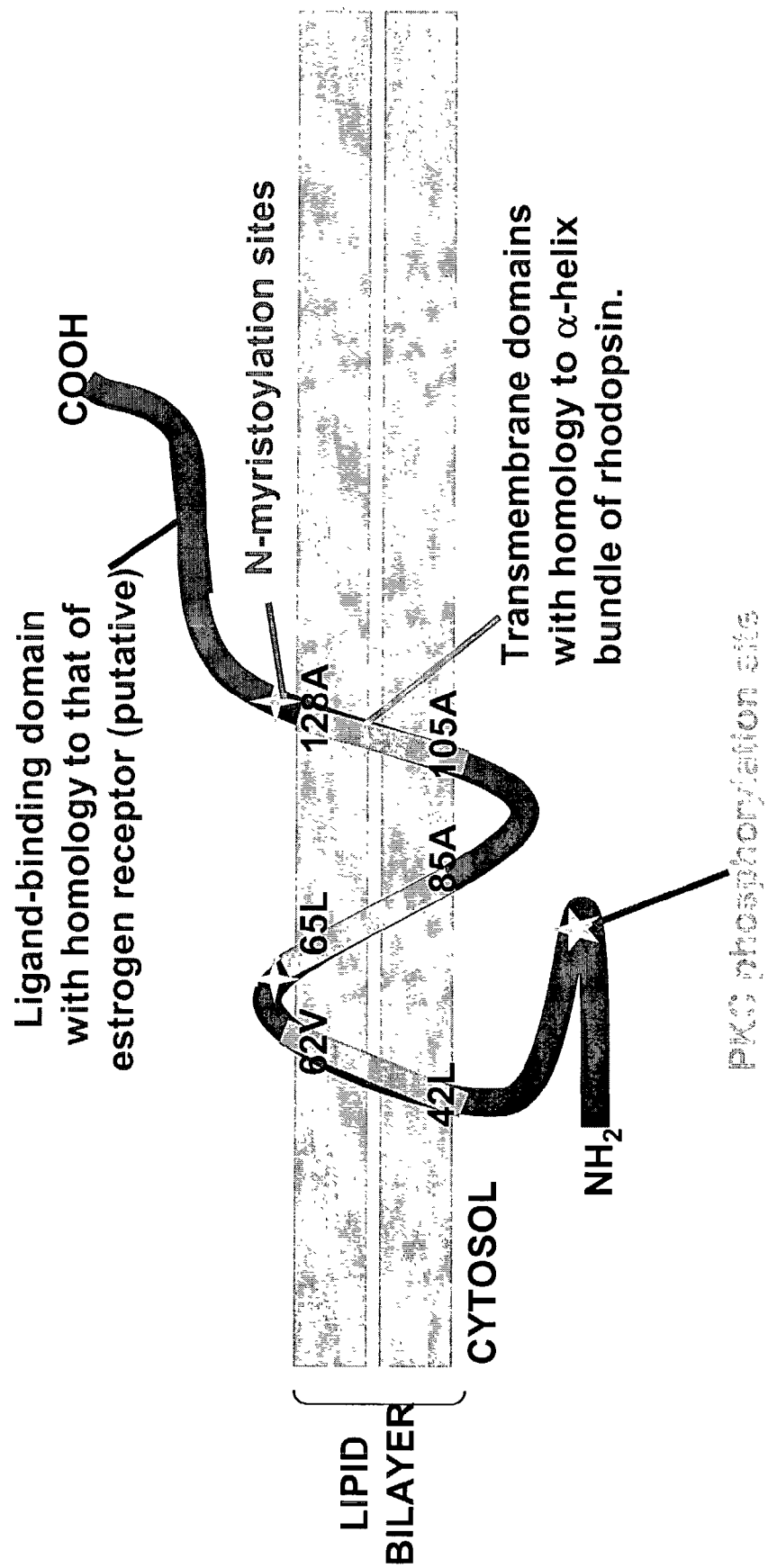
FIG. 1B is a schematic diagram illustrating the putative structure of the GDOX gene product.

The present invention is based on the discovery of a gene, GDOX, which is overexpressed in various human cancers. GDOX provides a novel target for treatment and detection of cancer. Moreover, the data described herein show that antibodies and anti-sense nucleotides directed against GDOX are effective in inhibiting proliferation of cancer cells derived from multiple tissues, including brain, breast, lung, colon and prostate. This invention thus provides GDOX-related molecules as diagnostic and therapeutic agents for the detection, monitoring and treatment of various cancers.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "GDOX related molecule" includes GDOX polypeptides, polynucleotides encoding GDOX polypeptides, polynucleotides complementary to those encoding GDOX polypeptides, antibodies that specifically recognize and bind GDOX polypeptides.

As used herein, "biological activity of GDOX" refers to the specific binding of GDOX to a GDOX binding partner, such as a GDOX receptor or antibody, to the expression of a GDOX polynucleotide, and to the growth regulatory effects of GDOX related molecules.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "tumor protein" is a protein that is expressed by tumor cells. Proteins that are tumor proteins also react detectably within an immunoassay (such as an ELISA) with antisera from a patient with cancer.

An "immunogenic polypeptide," as used herein is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1–30 amino acids, preferably 5–15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquila Biopharmaceuticals); MPL or 3d-MPL (Corixa Corporation, Hamilton, Mont.); LEIF; salts of calcium, iron or zinc; an insoluble suspension of acylated tyrosine; acylated sugars; cationically or aniomically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides that encode one or more GDOX polypeptides, such as polypeptides comprising amino acids 1–178, 19–21, 53–58, 62–65, 65–85, 105–128, 118–123, 129–178, 137–155, 139–141 or 159–178 of SEQ ID NO: 2, or a portion or other variant thereof. Preferred polynucleotides comprise at least 15 consecutive nucleotides, preferably at least 30 consecutive nucleotides and more preferably at least 45 consecutive nucleotides, that encode a GDOX polypeptide. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such GDOX polynucleotides can be useful as primers and probes for the amplification and detection of GDOX related molecules in tissue specimens.

Polynucleotides may comprise a native sequence (i.e., an endogenous sequence that encodes a GDOX polypeptide or a portion thereof) or may comprise a variant of such a sequence. Polynucleotide variants contain one or more substitutions, additions, deletions and/or insertions such that the immunogenicity of the encoded polypeptide is not diminished, relative to a native GDOX protein. Variants preferably exhibit at least about 70% identity, more preferably at least about 80% identity and most preferably at least about 90% identity to a polynucleotide sequence that encodes a native GDOX protein or a portion thereof Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 Methods in Enzymology vol. 183, Academic Press, Inc., San Diego, Calif.; Higgins, D. G. and Sharp, P. M. (1989) CABIOS 5:151–153; Myers, E. W. and Muller W. (1988) CABIOS 4:11–17; Robinson, E. D. (1971) Comb. Theor. 11:105; Santou, N., Nes, M. (1987) Mol. Biol. Evol. 4:406–425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native GDOX protein (or a complementary sequence).

Suitable "moderately stringent conditions" include pre-washing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formanide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding a GDOX protein may be obtained from a cDNA library prepared from tissue expressing a GDOX protein mRNA. Accordingly, human GDOX DNA can be conveniently obtained from a cDNA library prepared from human tissue. The GDOX protein-encoding gene may also be obtained from a genomic library or by oligonucleotide synthesis. Libraries can be screened with probes (such as antibodies to GDOX or oligonucleotides of at least about 20–80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding GDOX is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a GDOX protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a GDOX polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense Molecules

The antisense molecules of the present invention comprise a sequence substantially complementary, or preferably fully complementary, to all or a fragment of a GDOX gene. Included are fragments of oligonucleotides within the coding sequence of a GDOX gene. Antisense oligonucleotides of DNA or RNA complementary to sequences at the boundary between introns and exons can be employed to prevent the maturation of newly-generated nuclear RNA transcripts of specific genes into mRNA for transcription. Antisense RNA complimentary to specific genes can hybridize with the mRNA for that gene and prevent its translation. The antisense molecule can be DNA, RNA, or a derivative or hybrid thereof Examples of such derivative molecules include, but are not limited to, peptide nucleic acid (PNA) and phosphorothioate-based molecules such as deoxyribonucleic guanidine (DNG) or ribonucleic guanidine (RNG).

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphorarmidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos.: 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99–125, 1990. Formation of the triple helix would interrupt the ability of the specific gene to undergo transcription by RNA polymerase. Triple helix formation using myc-specific oligonucleotides has been observed. See: Cooney, M, et al. Science 241:456–459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S. and B. Lebleu, eds. CRC Press, Inc. Boca Raton Fla. 1993; Nucleic Acids in Chemistry and Biology Blackburn, G. and M. J. Gait, eds. IRL Press at Oxford University Press, Inc. New York 1990; and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

GDOX Polypeptides

GDOX polypeptides as described herein may be of any length. Additional sequences derived from the native protein and/or heterologous sequences may be present, and such sequences may, but need not, possess further ligand binding, immunogenic or antigenic properties. Preferred polypeptides comprise amino acid residues 1–178, 19–21, 53–58, 62–65, 65–85, 105–128, 118–123, 129–178, 137–155, 139–141 or 159–178 of SEQ ID NO: 2. Those skilled in the art will appreciate that other portions or variants thereof will be useful in the treatment and detection of cancer.

Immunogenic polypeptides may generally be identified using well known techniques, such as those summarized in Paul, Fundamental Immunology, 4th ed., 663–665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

A GDOX polypeptide of the invention can comprise a variant of a native GDOX protein. A polypeptide "variant," as used herein, is a polypeptide that differs from a native GDOX protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence, have been removed. Other preferred variants include variants in which a small portion (e.g., 1–30 amino acids, preferably 5–15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

In some embodiments, the polypeptides are purified from the same subject to whom the composition will be administered. In these embodiments, it may be desirable to increase the number of tumor or infected cells. Such a scale up of cells could be performed in vitro or in vivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the polypeptides are purified, it may also be desirable purify several GDOX polypeptides to optimize the efficacy of a limited quantity of starting material.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluotoacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises a GDOX polypeptide and an immunogenic polypeptide. The immunogenic polypeptide can comprise, for example, all or a portion of an additional tumor protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons requited to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86–91, 1997).

Within preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Antibodies

The term "antibody" is used in the broadest sense and specifically covers single anti-GDOX monoclonal antibodies (including agonist, antagonist and neutralizing antibodies) and anti-GDOX antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to GDOX proteins and polypeptides. The most preferred antibodies will specifically bind to a GDOX protein and will not bind (or will bind weakly) to non-GDOX proteins and polypeptides. Anti-GDOX antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region. Preferred antibodies and antibody fragments of the invention specifically bind to one or both of the following portions of the GDOX protein:

| HASLRLRNLKNKIENKIES; | (SEQ ID NO:3) |
| KRTPMGLLLEALGQEQEAGS. | (SEQ ID NO:4) |

GDOX antibodies of the invention may be particularly useful in cancer diagnostic and prognostic assays, and imaging methodologies. Intracellularly expressed antibodies (e.g., single chain antibodies) may be therapeutically useful in treating cancers in which the expression of GDOX is involved, such as for example advanced and metastatic brain cancers, as well as cancers of the lung, breast, colon or prostate. Also useful in therapeutic methods for treatment of cancer are systemically administered GDOX antibodies that interfere with GDOX function or that target cells expressing GDOX for delivery of a toxin or therapeutic molecule. Such delivery of a toxin or therapeutic molecule can be achieved using known methods of conjugating a second molecule to the GDOX antibody or fragment thereof. Similarly, such antibodies may be useful in the treatment, diagnosis, and/or prognosis of other cancers, to the extent GDOX is also expressed or overexpressed in other types of cancer.

The invention also provides various immunological assays useful for the detection and quantification of GDOX polypeptides. Such assays generally comprise one or more GDOX antibodies capable of recognizing and binding a GDOX, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing GDOX are also provided by the invention, including but not limited to radioscintigraphic imaging methods using labeled GDOX antibodies. Such assays may be clinically useful in the detection, monitoring, and prognosis of GDOX expressing cancers.

Various methods for the preparation of antibodies are well known in the art. For example, antibodies may be prepared by immunizing a suitable mammalian host using a GDOX protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of GDOX may also be used, such as a GDOX GST-fusion protein. In another embodiment, a GDOX peptide may be synthesized and used as an immunogen.

The antibodies or fragments may also be produced, using current technology, by recombinant means. Regions that bind specifically to the desired regions of the GDOX protein can also be produced in the context of chimeric or CDR grafted antibodies of multiple species origin. Humanized or human GDOX antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmann et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535–539).

Fully human GDOX monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human GDOX monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of GDOX antibodies with a GDOX protein may be established by a number of well known means, including western blot, immunoprecipitation, ELISA, and FACS analyses using, as appropriate, GDOX proteins, peptides, GDOX-expressing cells or extracts thereof.

A GDOX antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the GDOX antibody can be selected in accordance with the intended use. For example, for therapeutic use, the second molecule can be a toxin or therapeutic agent. Further, bi-specific antibodies specific for two or more GDOX epitopes may be generated using methods generally known in the art. Homodimeric antibodies may also be generated by cross-linking techniques known in the art (e.g., Wolff et al., Cancer Res. 53: 2560–2565).

T Cells

Immunotherapeutic compositions may also, or alternatively, comprise T cells specific for a GDOX polypeptide. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation I(it, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a GDOX polypeptide, polynucleotide encoding a GDOX polypeptide and/or an antigen presenting cell (APC) that expresses such a GDOX polypeptide. The stimulation is performed under conditions and for a time sufficient to permit the generation of T cells that are specific for the polypeptide. Preferably, a GDOX polypeptide or polynucleotide is present within a delivery vehicle, such as a microsphere, to facilitate the generation of specific T cells.

T cells are considered to be specific for a GDOX polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a GDOX protein (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a GDOX polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to a GDOX polypeptide, polynucleotide or APC can be expanded in number either in vitro or in vivo. Proliferation of such T cells in vitro may be accomplished in a variety of ways. For example, the T cells can be re-exposed to a GDOX polypeptide, with or without the addition of T cell growth factors, such as interleukin-2, and/or stimulator cells. Alternatively, one or more T cells that proliferate in the presence of a GDOX polypeptide can be expanded in number by cloning. Methods for cloning cells are well known in the art, and include limiting dilution.

Pharmaceutical Compositions and Vaccines

The invention provides GDOX polypeptide, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317–321, 1989; Flexner et al., Ann. N.Y. Acad Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616–627, 1988; Rosenfeld et al., Science 252: 431–434, 1991; Kolls et al., Proc. Natl. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the GDOX related molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

APCs may generally be transfected with a polynucleotide encoding a GDOX polypeptide (or portion or other variant thereof) such that the GDOX polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456–460, 1997. Antigen loading of dendritic cells may be achieved by incubating dendritic cells or progenitor cells with the GDOX polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10–50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Diagnostic Methods

The invention provides a method for detecting cancer in a tissue comprising contacting the tissue with a molecule that recognizes and binds a GDOX molecule. The molecule can be, for example, an antibody directed against a GDOX peptide, or an oligonucleotide probe or antisense molecule directed against a GDOX nucleic acid molecule. The tissue can be from a mammal, such as human, bovine, equine, canine, feline, porcine, and ovine tissue. The tissue is preferably a human. The tissue can comprise a tumor specimen, cerebrospinal fluid, or other suitable specimen. In one embodiment, the method comprises use of an ELISA type assay that employs a GDOX antibody to detect the presence of GDOX in a specimen. Those skilled in the art will appreciate additional variations suitable for the method of detecting cancer in tissue through detection of a GDOX molecule in a specimen. This method can also be used to monitor GDOX levels in tissue of a patient undergoing treatment for cancer. The suitability of a GDOX-targeted therapeutic regimen for initial or continued treatment can be determined by monitoring GDOX levels using this method.

The invention additionally provides a method for identifying a molecule that inhibits proliferation of cancer cells. The method comprises contacting a candidate molecule with a GDOX molecule and determining whether the candidate molecule disrupts the biological activity of the GDOX molecule. Disruption of the biological activity of the GDOX molecule is indicative of a molecule that inhibits proliferation of cancer cells. Representative GDOX molecules include antibodies, proteins and nucleotides.

Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a GDOX protein or a GDOX gene or message, respectively. The kit can also include containers containing nucleotide(s) for amplification of a target nucleic acid sequence and/or a container comprising a reporter-means, such as a biotin-binding protein, e.g., avidin or streptavidin, bound to a detectable label, e.g., an enzymatic, florescent, or radioisotope label. The kit can include all or part of the amino acid sequence of FIG. 2, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Identification of a New Glioma-Associated cDNA

This example demonstrates the use of cDNA subtractive hybridization, representational difference analysis (RDA), and differential immuno-absorption (DIA) to identify gene products that are differentially expressed in glioblastoma tumor tissue versus normal brain tissue. Candidate clones from each of the subtractive approaches were then screened in multiple tumor and non-tumor human brain tissues using cDNA microarray hybridization (Liau, L. and Yang, I., Current Genomics. 3: 33–41, 2002), and genes with consistently higher levels of expression (>5-fold) in brain tumors versus normal brain were selected.

Methods

Tissue specimens. Tissue samples from human tumor and non-tumor brain specimens were procured from patients undergoing surgery or at autopsy at the University of California at Los Angeles Medical Center, with approval from the institutional review board. All tissues were immediately snap frozen in liquid nitrogen and stored at −80° C. until use. Adjacent specimens were examined by neuropathologists and histopathology confirmed.

Representational difference analysis. Glioblastoma multiforme (GBM) tumor tissue and non-tumor brain were taken from the same patient at different time points. The tumor specimen was obtained at surgical resection, and the contralateral normal white matter was obtained from the same patient when he died of progressive disease nine months later. Both specimens were similarly frozen in liquid nitrogen and stored at −80° C. Total RNA was extracted from 300 mg of each tissue using Trizol (Gibco-BRL) per the manufacturer's protocol. cDNA was synthesized from 30 µg total RNA by oligo(dT) priming using Superscript II as recommended by the manufacturer (Gibco-BRL). Representational difference analysis (RDA) of this cDNA was performed similar to previously published methods (Hubank, M. and Schatz, D., Nucleic Acids Research. 22: 5640–5648, 1994; Welford, S., et al., Nucleic Acids Research. 26: 3059–3065, 1998). Three rounds of RDA were carried out, and the tester:driver ratios for each consecutive round were 1:100, 1:500, and 1:5000, respectively. Subtracted RDA products were digested with DpnII and shotgun cloned into the BamHI site of pZErO (Invitrogen). Inserts were verified by 1.2% agarose gel electrophoresis and found to be between 500 and 1500 base pairs.

Differential immuno-absorption. Glioblastoma multiforme (GBM) tumor tissue was immediately snap frozen in liquid nitrogen at the time of surgery. Non-tumor brain was obtained from a surgical resection for trauma and similarly frozen. Tissue specimens from separate patients were used. Differential immuno-absorption (DIA) was performed using a method described previously (Liau, L., et al., Cancer Res. 60: 1353–1360, 2000). Briefly, both tissue specimens were homogenized in saline, drawing off the soluble material. The insoluble material was then re-extracted with a small amount of 1% SDS. Aliquots of tumor homogenate and normal brain homogenate were each linked to sepharose using CNBr activation. The remainder of the saline soluble GBM tumor homogenate was emulsified in complete Freund's adjuvant (CFA) and used to immunize rabbits; and the detergent fraction was used to boost the animals in incomplete Freund's adjuvant (IFA) to produce anti-GBM antiserum. This antiserum was passed through the GBM-sepharose column and anti-GBM antibodies were eluted off.

To select out antibodies that bind to normal brain antigens and non-specific antibodies, the eluate was then repeatedly cross-absorbed against a normal brain affinity column and normal human plasma. The final antibody preparation was then neutralized, concentrated, dialyzed, and biotinylated. These biotinylated antibodies were then used to screen a GBM cDNA expression library, which was constructed as previously described (Liau, L., et al., Cancer Res. 60: 1353–1360, 2000). Positive clones were isolated and subcloned into the pZL1 plasmid vector (Gibco-BRL) by in vivo excision. Inserts were verified by 1.2% agarose gel electrophoresis.

Sequence and structure analysis. The final difference products from RDA were digested with DpnII and cloned into the BamH1 site of pZErO-2 vector (Invitrogen). The subtractive clones from the DIA technique were subcloned into the pZL1 plasmid vector (Gibco-BRL) by in vivo excision. Double stranded plasmid DNA was prepared from both sets of vectors using miniprep columns (Qiagen), and sequenced with M13 and T7 universal primers (Promega) using a dsDNA cycle sequencing kit (Gibco-BRL) per manufacturer's protocol. Nucleotide sequences were compared with known sequences in GenBank using the BLAST program (Altschul, S. et al., Nucleic Acids Res. 25, 3389–3402, 1997), and structure analyses were performed on deduced amino acid sequences using PROFILE (Fischer, D. & Eisenberg, D., Protein Science 5, 947–955, 1996; Gribskov, M., et al., Proc. Natl. Acad. Sci. USA 84, 4355–4358, 1987) and PROSITE (Bairoch, A., et al., Nucl. Acids Res. 25, 217–221, 1997) searches.

Results

Twenty-three subtractive products were selected from the cDNA subtractive library, 21 genes identified using RDA, and 28 differentially expressed clones were isolated with DIA. Sequence analysis of these clones indicated that one common 1276 bp cDNA with a 15-residue poly(A)+ tail, which was designated GDOX, was independently identified using all three methods of subtractive cloning. Although no nucleic acid homologies to any previously characterized genes were initially detected following searches in publication databases, sequence identity was found with an unpublished mRNA (alias JM4, GenBank Accession #AJ005896) that was recently mapped by positional cloning of the proximal human X chromosome at Xp11.23 (Strausberg, R. L., J Pathol. 195: 31–40, 2001; Strom, T. M., et al., Nature Genetics. 19: 260–263, 1998).

The deduced amino acid sequence of this novel clone, designated GDOX, contains 178 amino acid residues with a predicted molecular mass of 19 kD. Amino acid sequence analyses of the predicted protein structure of GDOX in relevant databases (SwissProt, Brookhaven Protein Data Bank, ProDom, and GenPept) using PROFILE and PROSITE analyses identified no significant homology to any known proteins. However, the predicted GDOX structure did have transmembrane domains with 24% amino acid identity with the 7-α-helix bundle of rhodopsin (Z-score of 5.3 standard deviation units) and a possible ligand-binding region with 27% identity to that of the human estrogen receptor (Z-score=5.1). In addition, potential protein kinase C phosphorylation sites were predicted at residues 19–21 and 139–141, while N-myristoylation sites were suggested at residues 53–58 and 118–123 (FIGS. 1A–B).

FIG. 1A shows the nucleotide and deduced amino acid sequence of GDOX. The underlined region indicates the predicted GDOX open reading frame (ORF) with the corresponding amino acid sequence. The initiator codon (ATG) starts at nucleotide 17, and the stop codon (TAG) ends at 553. Predicted protein kinase C (PKC) phosphorylation sites are indicated in red, and possible N-myristoylation sites are shown in blue. FIG. 1B is a schematic diagram illustrating the putative structure of GDOX gene product.

Example 2

GDOX Expression in Human Brain Tumor Tissues

This example demonstrates differential expression of the GDOX gene in tumorigenic versus normal brain tissues via northern blot and in situ hybridization analysis using radiolabeled GDOX cDNA, and via western blot analysis using GDOX antibodies. The results show that GDOX is overexpressed in a variety of gliomas, GDOX is not expressed in normal brain or in other normal tissues examined, with the exception of expression in normal testis and very low levels in normal kidney. In addition, the increased expression is attributable to actual cellular overexpression, and not to tumor hypercellularity. The overexpression was found at both the protein and RNA levels.

Methods

Northern blot analysis. Tissue total RNA was extracted using Trizol reagent (Gibco-BRL) per manufacturer's instructions, and 10 μg/lane were separated on 1.2% denaturing agarose gels, transferred overnight to Hybond membranes (Amersham) using 10×SSC, and irreversibly fixed by UV cross-linking. Prehybridization and hybridization were performed at 65° C. in ExpressHyb solution (Clontech). $^{32}$P-labeled cDNA probes were generated from the plasmid DNA containing GDOX cDNA using random primers per manufacturer's protocol (NEB). After hybridization, membranes were washed (2×SSC plus 0.1% SDS at 37° C. for 20 min, followed by 0.2× SSC plus 0.1% SDS at 61° C. for 20 min), and exposed to X-ray film (Kodak) at 80° C. Blots were then stripped with 0.1% SDS at 100° C. for 15 minutes and re-probed with $^{32}$P-labeled ribosomal 18S cDNA in order to control for gel loading and RNA integrity.

In situ hybridization. In situ hybridization was performed using $^{35}$S-labeled riboprobes following previously published protocols (Kornblum, H. et al., J Neurosci Res 53:697–717, 1998; Kornblum, H., et al. Mol Brain Res 21: 107–114, 1994). Briefly, surgically resected human brain tissues (tumor and non-tumor) were rapidly frozen in isopentane directly from the operating room. Frozen tissues were sectioned on a cryostat at 20-μm thickness, post-fixed in 4% paraformaldehyde, washed, and stored at −75° C. Sections were washed, acetylated, defatted, and incubated with $^{35}$S-labeled sense or antisense GDOX cRNA probe ($10^7$ cpm/ml) at 60° C. overnight (18–24 h). Following RNAse A (20 μg/ml) treatment at 45° C., sections were washed in descending concentrations of SSC, air dried, and dipped for emulsion autoradiography in Kodak NTB2 (1:1 dilution). Following exposure to emulsion for 5 weeks, the slides were developed and counterstained with hematoxylin and eosin.

Western blot analysis. Polyclonal antibodies were raised against two synthetic peptides (GDOX sequences 137–155 and 159–178; SEQ ID NOS: 3 and 4, respectively) conjugated to KLH (Research Genetics, Huntsville, Ala.). The anti-GDOX IgG fractions were isolated using sepharose-bound peptide and eluted using borate buffer at pH 2.7. Human glioma and normal brain tissues were homogenized in PBS containing 1% SDS, and protein concentrations were determined using standard Bradford assays. Thirty micrograms of cell homogenate per lane were resolved through SDS/PAGE on 12% gels and electrophoretically transferred onto nitrocellulose membranes (Bio-Rad). Membranes were rinsed, blocked with 5% BSA, and then incubated with polyclonal rabbit anti-GDOX antibodies at room temperature for 1 hour, using antibody dilutions of 1:500 and 1:1000. Blots were then washed and probed with goat anti-rabbit secondary antibody conjugated to horseradish peroxidase (Vector Laboratories). Proteins were visualized using the Vector ABC Elite staining reagents (Vector Laboratories) per manufacturer's protocol.

Results

Figures 2A, 2B:
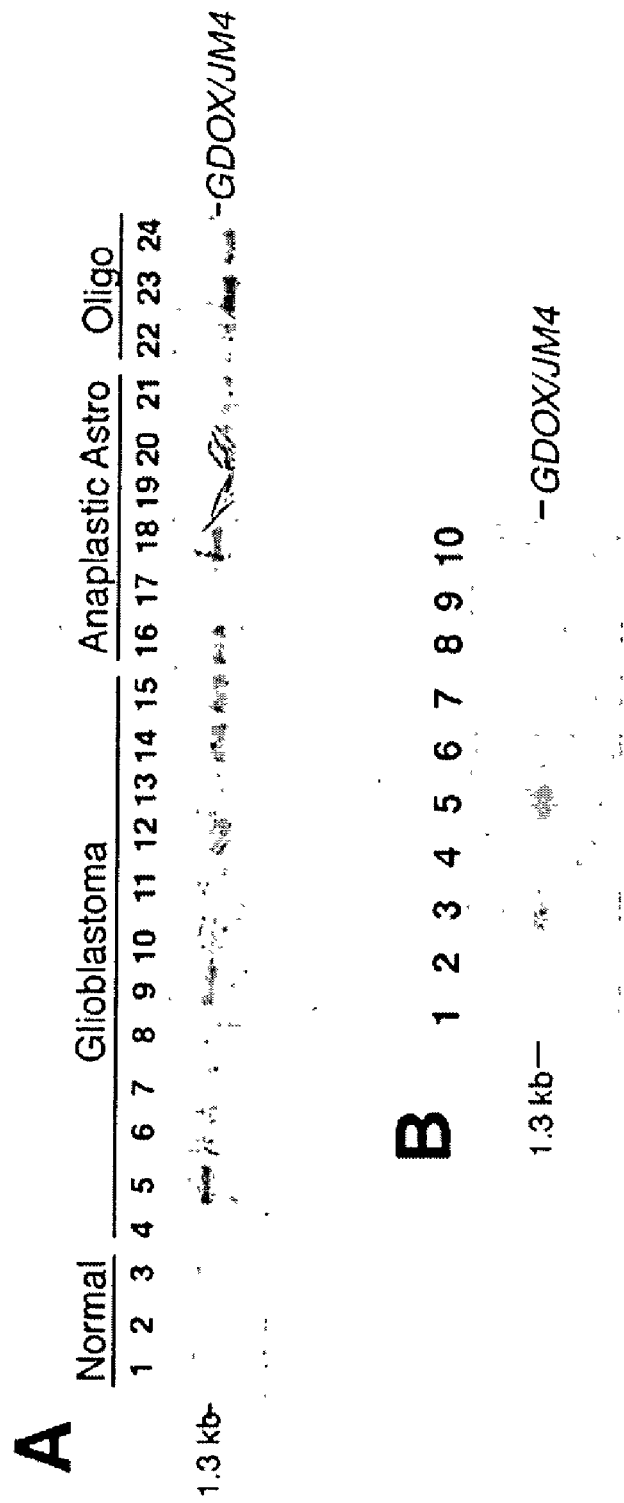
FIG. 2A displays the results of a northern blot analysis showing expression of GDOX mRNA in normal vs. tumorigenic brain tissues. Lanes 1–3 were non-tumorigenic brain tissues taken from a surgical resection for epilepsy (lane 1), surgical decompression for trauma (lane 2), and autopsy normal brain (lane 3). Lanes 4–24 were surgically resected brain tumor tissues that were pathologically confirmed to be glioblastomas (lanes 4–15), anaplastic astrocytomas (lanes 16–21), or oligodendrogliomas (lanes 22–24). The blot was exposed for 24 hours without intensifying screen.
FIG. 2B displays the results of a northern blot analysis showing expression of GDOX mRNA in various human peripheral organs. Tissue specimens were taken at autopsy from normal brain (lane 1), lung (lane 2), kidney (lane 3), skeletal muscle (lane 4), testes (lane 5), liver (lane 6), pancreas (lane 7), spleen (lane 8), heart (lane 9), and adrenal gland (lane 10). This blot was exposed for 2 weeks with intensifying screens. As a loading control, the same blots were reprobed with 18S cDNA and exposed for 1 hour without a screen.

The 1.3 kb transcript of GDOX was expressed in 19/21 different human gliomas and none of the normal brain specimens analyzed (FIG. 2A). The level of GDOX expression was found to be tumor-dependent, rather than grade-related. A panel of other human tissues was studied for GDOX expression and relatively low mRNA levels were detected in testes and kidneys upon extended exposure of the Northern blot (2 weeks), but no expression was seen in any other peripheral organs tested (FIG. 2B).

In situ hybridization with $^{35}$S-riboprobes generated using linearized plasmid-cDNA as templates from both strands was used with various tumor and non-tumor brain specimens. GDOX antisense riboprobe hybridized predominantly to hypercellular areas of tumor tissue and not normal brain tissue. The identity of the cells stained by the GDOX probe was supported by counterstaining with hematoxylin and eosin. Under high-power magnification, significantly increased GDOX hybridization was seen within the tumor cells compared to normal glial cells on a per cell basis, indicating that the increased expression pattern found in gliomas was due to actual cellular overexpression rather than tumor hypercellularity. Sense strand riboprobe generated from antisense strand cDNA was not observed to have specific hybridization, indicating that cellular hybridization obtained with the antisense probe was specific for GDOX mRNA.

Western blot analysis detected a single band of approximately 57-kd in all of the glioma tissues analyzed (8/8), while no corresponding bands were seen in normal brain specimens (0/3) (FIG. 3A). The same band was also seen in human testes and kidney tissues, but no other organs screened (FIG. 3B). Thus, western blots agreed with the expression pattern of GDOX seen by northern blot analysis.

Example 3

GDOX Subcellular Localization and Co-Expression with GFAP

Figures 4A, 4B:
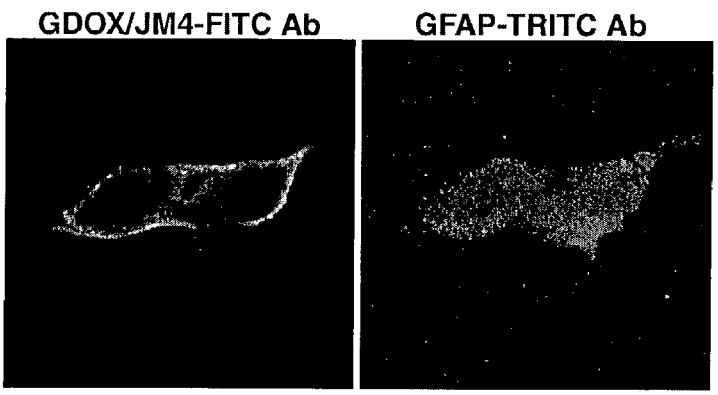
FIGS. 4A–B are photomicrographs showing cellular localization of GDOX (FIG. 4A) and GFAP (FIG. 4B) in U87 human glioblastoma cells. U87 cells were seeded on coverslips. Expressed GDOX was detected by immunofluorescence with an anti-GDOX peptide antibody, followed by staining with a FITC-conjugated secondary IgG. Expression of GFAP was detected with an anti-GFAP antibody, followed by staining with a TRITC-conjugated secondary antibody. Specificity of the primary antibody was confirmed by the lack of staining of secondary antibody alone. Original magnification, 400×.

This example describes the subcellular localization of GDOX and compares its expression to that of glial fibrillary acidic protein (GFAP). To determine the cellular localization of GDOX expression in U87 and primary human glioblastoma cells, immunofluorescence staining for the C-terminal end of GDOX was performed using the GDOX peptide antibodies described above in Example 2. The GDOX protein was localized primarily to the plasma membrane (FIG. 4A), suggesting that it is a transmembrane protein, as deduced from its computer-generated predicted structure (FIGS. 1A–B). To assess for co-expression of GDOX within glioma cells, double immunofluorescence staining was performed with the addition of an anti-GFAP monoclonal antibody. U87 cells were seeded on coverslips. Expressed GDOX was detected by immuno-fluorescence with an anti-GDOX peptide antibody, followed by staining with a FITC-conjugated secondary IgG. Expression of GFAP was detected with an anti-GFAP antibody, followed by staining with a TRITC-conjugated secondary antibody. Specificity of the primary antibody was confirmed by the lack of staining of secondary antibody alone. GFAP expression was found mainly in the cytoplasm (FIG. 4B), although both GDOX and GFAP co-localized to the same cells.

Figures 5A, 5B:
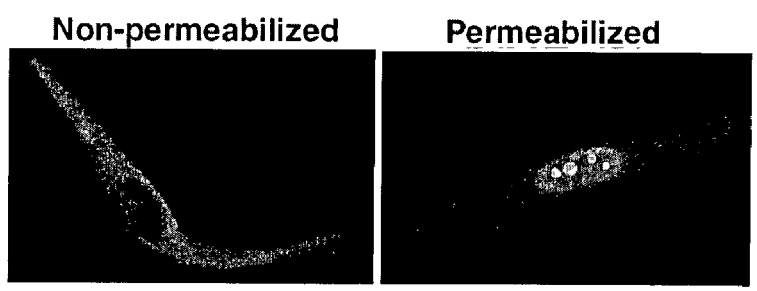
FIGS. 5A–B are photomicrographs showing cellular localization of GDOX, as assayed by immunofluorescence confocal microscopy of non-permeabilized (FIG. 5A) or permeabilized (FIG. 5B) primary human glioblastoma cells. Original magnification, 400×.
Figures 6A, 6B:
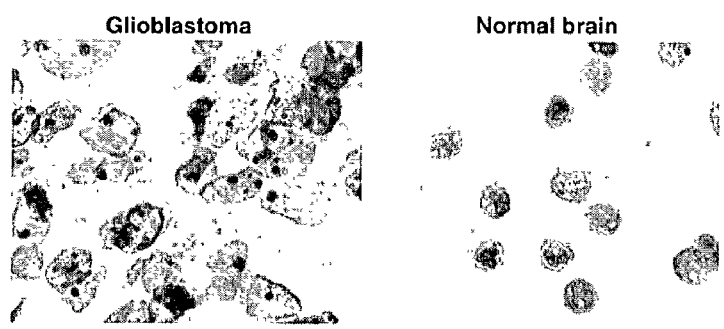
FIGS. 6A–B is a photomicrograph showing immunohistochemistry staining using GDOX antibody for analysis of human tumor (FIG. 6A) versus non-tumor (FIG. 6B) brain tissue. Note nucleolar subcellular localization of GDOX in glioblastoma tissues. Original magnification, 200×.

In additional experiments, subcellular localization was assayed by immunofluorescence microscopy of permeabilized and non-permeabilized cells. FIGS. 5A–B are photomicrographs showing cellular localization of GDOX, as assayed by immunofluorescence confocal microscopy of non-permeabilized (FIG. 5A) or permeabilized (FIG. 5B) primary human glioblastoma cells. In the permeabilized cells, the GDOX protein was localized primarily to the nucleolus, suggesting cellular trafficking from the plasma membrane to the nucleus. This nucleolar localization was also confirmed by immunohistochemical staining of human glioblastoma tissue sections. FIGS. 6A–B is a photomicrograph showing immuno-histochemistry staining using GDOX antibody for analysis of human tumor (FIG. 6A) versus non-tumor (FIG. 6B) brain tissue. Note nucleolar subcellular localization of GDOX in glioblastoma tissues.

Example 4

GDOX Chromosomal Localization

In this example, somatic cell hybrid mapping was used to map the genomic location of GDOX. A commercially produced somatic cell hybrid mapping panel consisting of various mouse-human and hamster-human hybrids was obtained from Coriell Cell Repositories (Camden, N.J.). Southern blot analysis was performed with $^{32}$P-labeled cDNA probes made from plasmid DNA containing the GDOX clone using random primers per manufacturer's protocol (NEB).

FIG. 7 displays the results of Southern blotting of GDOX cDNA to human chromosomal DNA in somatic cell hybrid panel. DNA hybridization revealed a band of predicted size with human genomic DNA and with DNA from the somatic cell hybrid NA10324, which was the only hybrid represented in this mapping panel that contained the human X chromosome. Therefore, the GDOX gene appears to be on human chromosome X.

Example 5

Biological Effects of GDOX Expression in Transfected Glial Cells

To determine if GDOX plays a role in glial cell tumorigenesis and/or proliferation, sense and antisense GDOX constructs were assembled and transfected into murine and human glial cell lines. A conditionally immortalized murine glial cell line (CIMO; Bronstein, J., et al., J. Neurochem. 70: 483–491, 1998; Jat, P., et al., Proc. Natl. Acad. Sci. USA. 88: 5096–5100, 1991) was used to test whether overexpression of GDOX could induce neoplastic transformation of non-tumorigenic glial cells in vitro. CIMO cells were derived from primary cultures of brains obtained from H-2Kb-tsA58 transgenic mice.

Cell culture and transfection. A conditionally immortalized glial cell line (CIMO) was derived from primary brain cultures of H-2Kb-tsA58 transgenic mice (Charles River Laboratories, Wilmington, Mass.) as described previously (Bronstein, J., et al., J Neurochem 70: 483–491, 1998; Jat, P. et al., Proc. Natl. Acad. Sci. USA 88: 5096–5100, 1991). These glial cells contain the temperature-sensitive SV40 large T-antigen oncogene under the control of an interferon-γ-inducible promoter, which allowed rapid growth under permissive conditions (33° C. in the presence of interferon-γ) but not under non-permissive conditions (37° C. in the absence of interferon-γ). These cells were passaged and maintained in T75 flasks in DMEM supplemented with 5% fetal calf serum (FCS) in 5% $CO_2$ either at 33° C. with IFN-γ(permissive conditions) or at 37° C. without INF-γ (non-permissive conditions). The human glioblastoma cell line U87 was obtained from the American Type Culture Collection (Rockville, Md.) and maintained in DMEM supplemented with 5% FCS, 2 mM L-glutamine, and antibiotic drugs (100 U/ml penicillin and 100 μg/ml streptomycin) in 5% $CO_2$ at 37° C.

Both the murine and human cell lines were transfected with the GDOX cDNA fragment cloned into the pBK-CMV expression vector in either sense or antisense orientation as described below. For construction of the sense vector, the full-length 1276-bp GDOX cDNA in the pZL1 vector (Gibco-BRL) was digested with NotI and SalI enzymes and subcloned into the NotI and SalI sites of pBK-CMV (Gibco-BRL). To construct the antisense vector, the pZL1 vector containing the full-length GDOX cDNA was digested with SmaI and XbaI enzymes, and the removed fragment was subcloned in antisense orientation into the XbaI and SmaI sites of pBK-CMV. For controls, pBK-CMV (empty vector) and pBK-CMV-GFAP (random sequence) plasmids were also used to transfect cells. Transfection of CIMO and U87 cells was performed using DOTAP per manufacturer's instructions when the cells reached 80% confluence. One day after transfection, cells were subcultured and selected in serum-supplemented medium in the presence of 400 μg/ml of G-418 (Gibco-BRL). This medium first was changed 2 days later and then every 3–4 days thereafter. After 14 days, colonies of G418-resistant cells were checked for the presence of GDOX expression by northern blot analysis as described above. The presence or absence of GDOX expression in the modified cells was confirmed by western blot analysis (FIG. 8).

The morphological phenotype of sense, antisense, and control-transfected U87 cells was examined. Phase-contrast microscopy indicated that the glial cells transfected with antisense-GDOX did not spread as well as the control cells and maintained a more rounded morphology (FIGS. 9A–B). In contrast, the sense-GDOX transfected cells appeared to have more cytoplasmic processes and grew in larger patches than the control cells. The wild-type control U87 cells were highly refractile and grew in large patches with cytoplasmic processes (FIG. 9A). The antisense GDOX-transfected cells did not grow well and had a more rounded morphology (FIG. 9B).

Growth rates of the different types of transfected cells were measured using [$^3$H]thymidine incorporation. Cells were plated in 12-well plates (Corning) at a density of $5 \times 10^4$ cells per well in 2 ml of DMEM supplemented with 5% FCS. After 5 days, the medium was changed to fresh DMEM medium containing [$^3$H]thymidine (1 µCi/ml, specific activity 0.4 Ci/mmol) and incubated for 24 hours. The cells were then washed with ice-cold phosphate-buffered saline (PBS), and the DNA was precipitated with 5% trichloroacetic acid and solubilized in 0.1% SDS. Incorporated radioactivity was determined with a liquid scintillation counter. Assays were performed three times, each time in four wells per condition and counted in triplicate. Differences in proliferation rates were statistically analyzed using the Student's t-test.

Figure 10:
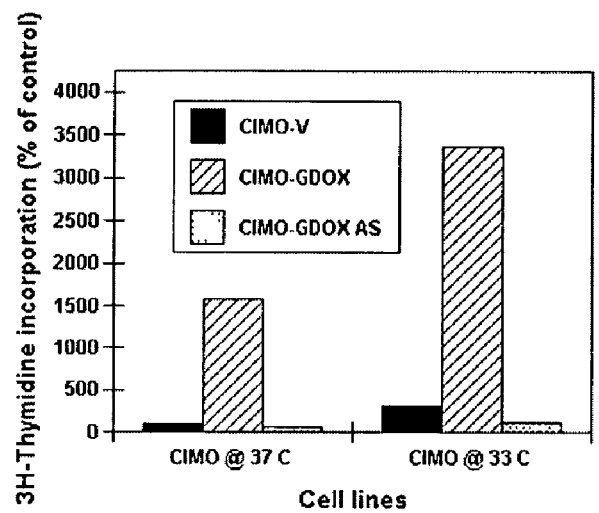
FIG. 10 is a bar graph showing the effects of GDOX overexpression on the proliferation of glial cells in vitro. In vitro growth rates of pBK-CMV-GDOX-transfected and control-transfected murine CIMO cells were measured by [$^3$H]thymidine incorporation assay. Results in counts per minute (cpm) were normalized in terms of percentage of empty-vector (pBK-CMV) transfected cell proliferation under non-permissive conditions (37° C.). The empty-vector control (CIMO at 37° C.) cpm was set at 100% in each run, and all other counts in each experiment were normalized to this value. The results shown are combined from three independent experiments, using triplicate wells each. Bars represent mean values +SD.

As shown in FIG. 10, CIMO cells transfected with GDOX cDNA had a markedly increased proliferative capacity under both permissive (33° C.) and unpermissive (37° C.) conditions. Compared to empty-vector control-transfected cells cultivated under similar conditions, GDOX-transfected CIMO cells exhibited a 9.5-fold (at 37° C., p=0.0006) to 15-fold (at 33° C., p<0.0001) increase in growth rate (FIG. 10). Results, in counts per minute (cpm), were normalized in terms of percentage of empty-vector (pBK-CMV) transfected cell proliferation under non-permissive conditions (37° C.). The empty-vector control (CIMO at 37° C.) cpm was set at 100% in each run, and all other counts in each assay were normalized to this value. The results shown are combined from three independent assays, using triplicate wells each.

Figure 11:
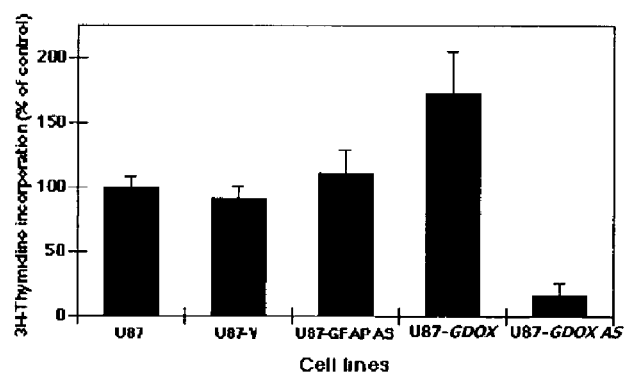
FIG. 11 is a bar graph showing the growth modulation effect of GDOX in human glioma cell line U87 in vitro. Parental U87 or U87 cells transfected with empty vector (U87-V), a vector containing a random antisense (U87-asGFAP), sense GDOX (U87-GDOX), or antisense GDOX (U87-asGDOX) were assayed by [$^3$H]thymidine incorporation. Results are normalized in terms of percentage of control wild-type U87 cell proliferation, which was set at 100%.

A significant, although less marked, 2-fold increase in cell proliferation was also seen in human U87 glioblastoma cells transfected with sense GDOX cDNA, while antisense GDOX-transfection of U87 cells significantly suppressed tumor cell growth to 17% of wild-type controls. FIG. 11 is a bar graph showing the growth modulation effect of GDOX in human glioma cell line U87 in vitro. Parental U87 or U87 cells transfected with empty vector (U87-V), a vector containing a random antisense (U87-asGFAP), sense GDOX (U87-GDOX), or antisense GDOX (U87-asGDOX) were assayed by [$^3$H]thymidine incorporation. Results are normalized in terms of percentage of control wild-type U87 cell proliferation, which was set at 100%.

Example 6

Biological Effects of Anti-GDOX Antibody on Multiple Human Cancers in vitro

This example demonstrates that antibodies targeted to the GDOX gene product have antitumor effects on human cancer cells in vitro. Early-passage primary human glioblastoma cells were incubated with increasing concentrations of GDOX polyclonal antibody for 4 days, stained with trypan blue, and counted. The morphological phenotype of the treated and control cells were examined. Phase-contrast microscopy indicated that the tumor cells treated with the GDOX antibody did not grow and spread as well as the control cells. Furthermore, anti-GDOX antibody-treated tumor cells from various different types of human cancers (brain, lung, breast, colon and prostate) exhibited a dose-dependent decrease in cellular proliferation as measured by standard [$^3$]thymidine incorporation analysis.

FIGS. 12A–D are bar graphs showing the growth suppressive effect of a specific anti-GDOX antibody in human tumor cell lines: FIG. 12A, ES-UCLA (primary glioblastoma); FIG. 12B, SKBR3 (breast adenocarcinoma); FIG. 12C, A549 (lung carcinoma); and FIG. 12D, Du145 (prostate cancer). Results were normalized in terms of percentage of control proliferation, with the control cells receiving equal volumes of heat-inactivated anti-GDOX antibody or a control antibody.

Example 7

Correlation of Cancer Patient Survival with Overexpression of GDOX

Figure 13:
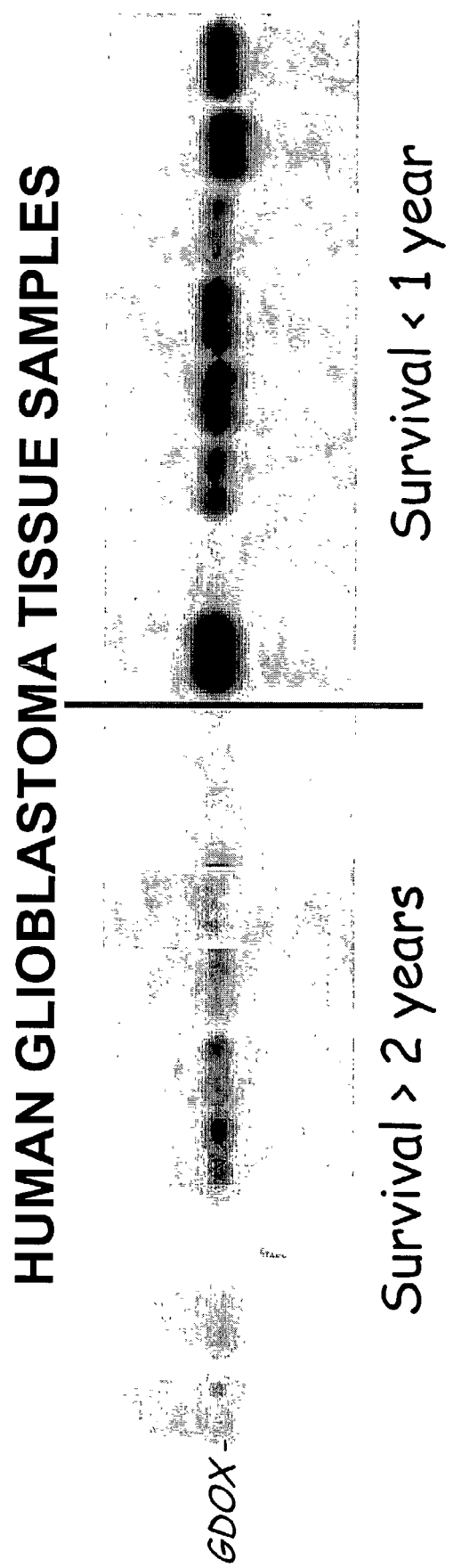
FIG. 13 displays the results of a northern blot analysis of the correlation of survival with overexpression of GDOX. Samples from human glioblastoma patients were probed with a GDOX cDNA and relative amounts of GDOX mRNA expression were compared between samples from patients surviving more than 2 years (left panel) and from patients surviving less than one year (right panel). Substantial overexpression of GDOX protein was observed in patients with shorter survival times.

This example demonstrates that overexpression of GDOX is correlated with survival in human glioblastoma patients. FIG. 13 displays the results of a northern blot analysis of samples from human glioblastoma patients that were probed with a GDOX cDNA. Relative amounts of GDOX mRNA expression were compared between samples from patients surviving more than 2 years (left panel) and from patients surviving less than one year (right panel). Substantial overexpression of GDOX protein was observed in patients with shorter survival times. In addition to supporting the use of GDOX and its products as a diagnostic and therapeutic target for cancer, these data show that GDOX expression can also be useful in determining prognosis and monitoring disease progression and/or response to therapy.

Example 8

Characterization of Molecular Pathways by Which GDOX Functions in Tumor Cells

Subcellular localization studies. GDOX protein appears to be localized to the plasma membrane, which is consistent with its predicted structure as a transmembrane protein by computer analysis of the GDOX primary sequence, and supports the finding of GDOX antibody-induced modulation of an accessible membrane protein (FIGS. 12A–D). However, when localization was assayed by immunofluorescence confocal microscopy of permeabilized primary glioma cells (FIGS. 5A–B) and immunohistochemistry of cut human glioblastoma tissue sections (FIGS. 6A–B), GDOX was primarily found in the nucleolus. These data suggest that GDOX may be a plasma membrane protein that is translocated to the nucleolus upon activation. Further determination of the subcellular localization and orientation of this protein in tumor cells can be accomplished by use of GFP- and HA-tagged GDOX constructs transiently expressed in human tumor cells.

Protein kinase C (PKC) phosphorylation studies. As shown in FIG. 1A above, computer-assisted motif analysis revealed the presence of a phosphorylation site for the serine/threonine PKC at the NH$_2$ terminus of the GDOX predicted protein, at amino acids 139–142. In view of the observation that the predicted GDOX protein harbors a consensus recognition motif for protein kinase C (PKC), protein phosphorylation may be a regulatory mechanism for GDOX function in human brain tumor cells.

Phosphorylation of endogenous GDOX protein in cell-free extracts. To characterize GDOX phosphorylation, label incorporation from [γ-$^{32}$P]ATP in U87 cell-free extracts to the endogenous GDOX protein is examined. To study $^{32}$P incorporation, cell extracts (150 μg of protein in a volume of 100 μl) are prepared in TGED buffer and supplemented with [γ-$^{32}$P]ATP (10 μM; 0.1 μCi) in the presence or absence of MgCl$_2$ (0–10 mM). After incubation at 30° C. for 20 minutes, the reactions are terminated by adding 300 μl of ice-cold TBS containing 10 mM EDTA, and the GDOX protein present in the extracts is immunoprecipitated. After electrophoresis of solubilized immunoprecipitates on 12% polyacrylamide gels, the gel is dried and exposed to X-ray film to visualize the $^{32}$P-labeled GDOX protein. A duplicate of kinase assays with 50 μg of protein, 10 μM unlabeled ATP instead of [γ-$^{32}$P]ATP is processed for western blotting of the GDOX protein as a control.

Phosphorylation of GDOX protein in human brain tumor cells. To demonstrate that phosphorylation of GDOX is physiologically relevant, one can confirm that the modification occurs in intact cells. To this end, human tumor cell lines are metabolically labeled with [$^{32}$P]P, followed by immunoprecipitation of the GDOX protein, SDS-PAGE, and autoradiography. Tumor cells are cultured in 25-cm$^2$ flasks, washed with phosphate-deficient DMEM (Life Technologies, Inc.) and incubated for 6 hours with the same medium containing [$^{32}$P]P, (10 μCi/ml) for 6 hours. The radiolabeling is terminated by washing the cells twice with ice-cold TBS. After trypsinization, cells are lysed in 0.5 ml of TBS containing 0.5 mM phenylmethylsulfonyl fluoride, 50 mM sodium fluoride, 0.5 mM sodium vanadate, and 1% NP40. The supernatants recovered by centrifugation are immunoprecipitated with GDOX antibodies. The immuno-complexes are resolved on $^{12}$% SDS-PAGE gels, and the gels are dried and subjected to autoradiography.

Purified PI(C (Calbiochem) is used to phosphorylate purified recombinant GDOX protein according to published protocols (Stivenugopal, K., et al., Cancer Research. 60: 282–287, 2000).

Example 9

Identification of Other Proteins that Interact with GDOX.

Western blot analysis of GDOX in human glioma tissues detected a predominant 57-kD band (FIG. 3A), although the predicted protein size for GDOX is only 19-kD. This may be due to post-translational modifications, dimerization/trimerization, or close association of GDOX with other proteins. The yeast two-hybrid system can be used to identify associated proteins that may interact with GDOX.

Yeast two-hybrid analysis. A yeast two-hybrid screening method (Tiwari-Woodruff, S. K., et al., J Cell Biology. 153: 295–305, 2001) is used to identify proteins that interact with GDOX. The entire GDOX ORF is subcloned into pGBT9 (Matchmaker system; CLONTECH). The Saccharomyces cerevisiae Hfc7-competent strain is transformed with pGBT9-GDOX using the lithium acetate method and used as the "bait" to screen a pGAD GH cDNA library made from mRNA derived from human glioblastoma tissues taken at surgical resection. Two reporter genes for interacting proteins are contained in the Hfc7 strain: HIS3 and β-galactosidase (β-gal). Transformants which express interacting proteins will grow on histidine-dependent medium (HIS-). Positive clones are transferred to sterile Whatman filters, placed on selection Trp-/Leu-/His-minimal SD medium agar, incubated for 1–3 hours at 30° C., and fixed by freezing in liquid nitrogen. Filters are then placed onto filter paper pre-soaked in buffer Z, supplemented with 50 mM β-mercaptoethanol and 0.07 mg/ml 5-bromo-4-chloro-3-indolyl-β-D-galactopyranoside (Sigma-Aldrich). Filters are incubated at 30° C. and monitored for the appearance of blue colonies. Plasmids from positive yeast colonies are isolated by a Yeastmaker kit (CLONTECH).

Plasmids isolated from positive colonies are individually cotransformed with GDOX bait cDNA and plated on HIS-SD medium to select for HIS3 reporter activation. Clones replated onto HIS-plates are then assayed for β-gal activity as described above. pGAD GH plasmids from the cured clones are rescued into E. coli and sequenced. Co-transformants are assayed for their ability to grow on HIS-medium and for β-gal activity (Ingley, E., et al., FEBS. 459: 69–74, 1999).

Co-Immunoprecipitation. The association of candidate proteins that interact with GDOX is then confirmed by co-immunoprecipitation studies. For co-immunoprecipitations, tumor cells are lysed in 25 mM Tris-HCl, pH 7.5, 120 mM NaCl, 1% NP-40, 5 mM EDTA, 25 mM NaF, 25 mM β-glycerol phosphate, 1 mM vanadate, and 1 mM benzamidine, then centrifuged at 1000×g for 5 minutes. The supernatants are incubated with GDOX antibody, collected with protein A beads, then immunoblotted with anti-GDOX or antibodies to the interacting protein(s) detected by yeast two-hybrid screening. Protein signals are detected by enhanced chemiluminescence (Amersham).

Example 10

Determining Sensitivity to Estrogen Antagonists

As shown in FIGS. 1A–B above, the predicted protein for GDOX has a possible ligand-binding region with homology to that of the human estrogen receptor. Tamoxifen ((Z)-2[p [(1,2-diphenyl-1-butenyl)phenoxyl]-N,N-dimethylamine citrate), a synthetic, non-steroidal anti-estrogen with relatively low toxicity that is used extensively in the treatment of breast cancer, has received interest as a possible therapeutic agent in the treatment of brain cancer. At high doses, orally administered tamoxifen has been shown to be of benefit in some patients with malignant gliomas (Couldwell, W. T., et al., Clin Cancer Res. 2: 619–622, 1996). However, unlike the cases of breast cancer, tamoxifen does not seem to act by competitive inhibition of estrogen receptor-mediated signaling of cell proliferation, as human glioblastoma cell lines (U87, U373, and U138) responsive to tamoxifen cytotoxicity have been found to lack detectable estrogen receptor expression and showed no mitogenic response to estradiol. The mechanism of growth inhibition by tamoxifen in human malignant gliomas does not involve an estrogen receptor-mediated process, but may instead result from interference with PKC activity (Pollack, I. F., et al., Cancer Research. 50: 7134–7138, 1990). Curiously, the relatively selective PKC inhibitor, staurosporine, appears to have a differential suppressive effect on glioma cell lines than does tamoxifen (Baltuch, G., et al., Neurosurgery. 33: 495–501, 1993), suggesting that tamoxifen-induced inhibition of human glioblastoma cell growth may involve additional mechanisms besides direct PKC inhibition. This may help to explain why the sensitivity of tamoxifen treatment for malignant gliomas in vivo cannot be predicted by either estrogen receptor expression or PKC activity (Puchner, M. J. A., et al., Acta Neurochir. 143: 563–573, 2001).

In view of the putative estrogen-binding domain on GDOX, an estrogen antagonist such as tamoxifen may affect human glioblastoma cells via a GDOX-mediated cellular mechanism, and GDOX overexpression may be a useful predictor of tamoxifen sensitivity, or of sensitivity to other estrogen antagonists. The U87 human glioblastoma cells stably transfected with sense and antisense GDOX cDNA (see FIG. 8) can be used to test tamoxifen sensitivity in GDOX-overexpressing tumors. The cell lines are maintained in DMEM containing 2% L-glutamine, supplemented with 15% FCS (Life Technologies), in 25-cm$^2$ flasks at a temperature of 37° C., a minimum relative humidity of 95% air, and atmosphere of 5% $CO_2$. For assays, exponentially growing cells are detached from the culture flasks using EDTA-trypsin and cell viability confirmed by trypan blue exclusion. Triplicate cultures for each dose of tamoxifen to be tested in each assay are inoculated into 96-well plates at a density of 5×10$^3$ cells per 100 μl medium per well. Cultures are allowed to stabilize for 24 hours and then exposed to serial dilutions of tamoxifen (Sigma) at 0, 5, 10, 15, 20, 25, 30, 35, and 40 μM tamoxifen:

| Dose of tamoxifen (μM) | Parental U87 | U87-sense GDOX | U87-antisense GDOX |
| --- | --- | --- | --- |
| 0 | 9 wells | 9 wells | 9 wells |
| 5 | 9 wells | 9 wells | 9 wells |
| 10 | 9 wells | 9 wells | 9 wells |
| 15 | 9 wells | 9 wells | 9 wells |
| 20 | 9 wells | 9 wells | 9 wells |
| 25 | 9 wells | 9 wells | 9 wells |
| 30 | 9 wells | 9 wells | 9 wells |
| 35 | 9 wells | 9 wells | 9 wells |
| 40 | 9 wells | 9 wells | 9 wells |

Incubations are carried out for a total of 4 days, in final volumes of 200 μl per well. Thus, untreated or 4-day tamoxifen-treated samples are used for the following three sets of assays (3 wells per assay). Typically, each assay is carried out at least three times.

i. Cellular localization of endogenous GDOX in parental and transfected U87 cells is carried out as described above. Cells are seeded on coverslips following treatment with the various doses of tamoxifen. Expressed GDOX is detected by immunofluorescence with anti-GDOX antibody, followed by staining with a FITC-conjugated secondary antibody.

ii. Cellular PKC activity is assessed as described above, using incorporation of [$\gamma^{32}$P]ATP as a measure of PKC phosphorylation in the parental and GDOX-transfected U87 cells following treatment with tamoxifen.

iii. Cell proliferation assays are performed by [$^3$H]thymidine incorporation as previously described (Liau, L., et al., Cancer Res. 60: 1353–1360, 2000; Lu, R. and Serrero, G., Proc Natl Acad Sci USA. 97: 3993–3998, 2000). Briefly, after 4 days of treatment with the various doses of tamoxifen, the cell medium is changed to fresh DMEM medium containing [$^3$H]thymidine (1 μCi/ml, specific activity 0.4 Ci/mmol) and incubated for 24 hours. The cells are washed with ice-cold PBS, and the DNA precipitated with 5% trichloroacetic acid and solubilized in 0.1% SDS. Incorporated radioactivity is determined with a liquid scintillation counter.

If tamoxifen has an effect on GDOX-mediated cell signal transduction, then ligand-binding to GDOX would cause differential subcellular localization or phosphorylation of the GDOX protein. Furthermore, tamoxifen treatment may cause a differential response in cell growth inhibition in sense GDOX-transfected U87 cells expressing high levels of GDOX versus antisense GDOX-transfected cells that do not express GDOX. Repeated-measures analysis of variance is used to compare the results between the different cell lines at each treatment dose.

Example 11

Disrupting GDOX Promotion of Tumorigenesis

This example describes various assays that can be used to clarify mechanisms by which GDOX promotes tumorigenesis. These assays can also be used to test the ability of a candidate therapeutic directed against GDOX or one of its gene products to disrupt the tumorigenic effects of GDOX overexpression. Both in vitro and in vivo assays can be employed.

As shown in the preceding examples, U87 human glioblastoma cells can be stably transfected with sense and antisense GDOX cDNA (FIG. 8). These cell lines can be used to analyze how GDOX promotes tumorigenesis and also to assay efficacy of therapeutic agents directed against GDOX or one of its gene products. Wild-type parental U87, U87-V (empty vector control), U87-antisense GFAP (random antisense control), U87-sense GDOX, and U87-antisense GDOX are analyzed using the following assays:

i. Cell proliferation assays. Cells (1×10$^5$ cells/well) are counted with a hemocytometer and seeded into 6-well plates (Costar) in 2 ml of medium and the appropriate selection agent (400 μg/ml G418). The cells are plated in triplicate and allowed to grow for varying time points (1, 2, 4, 6, 8, and 10 days). At each time point, the wells are rinsed twice in PBS and stained with 0.1% crystal violet. The cells are counted in triplicate for each cell line using a microscope with cell-counting software. The cell number is then plotted against culture times. Cellular proliferation of each of the cell lines can also be measured using the MTT assay as described by the manufacturer (Roche Diagnostics) and by [$^3$H]thymidine incorporation assay as described above.

ii. Cell cycle analysis. Flow cytometric analysis of the cell cycle distribution for log phase GDOX sense/antisense transfected cells and control cells is performed as described previously (Li, D. M. and Sun, H. et al., Proc Natl Acad Sci USA. 95: 15406–15411, 1998; Ge, S., et al., Clin Cancer Res. 6: 1248–1254, 2000; Huang, R. P., et al., Cancer Research. 58: 5089–5096, 1998). Briefly, parental U87 and GDOX-transfected cells are plated at equal density (4×10$^5$ cells) and maintained in culture for 3 days in DMEM+10% FBS. The medium is changed daily. 4-day-old cells are harvested when they are 70–80% confluent. Cells are trypsinized and inactivated in DMEM with 10% FBS, centrifuged for 5 min at 800 rpm, resuspended in PBS and counted. 2×10$^6$ cells are collected and fixed in 3 ml of ice-cold 70% ethanol for 30 min on ice and stored at 4° C. For flow cytometric analysis, ethanol is removed by centrifugation at 450×g for 5 min at room temperature, the supernatant decanted, and the cell pellets washed twice with ice-cold PBS. The cells are stained with propidium iodine (PI) by incubation in 1 ml of a PI/RNase mixture (50 μg/ml PI+5 U/ml RNase A in PBS) for 30 min at room temperature. The DNA content in the cells is analyzed using a FACS (Becton-Dickinson).

iii. Cell attachment assays. Attachment assays are performed as previously described (Rempel, S. A., et al., J Neuro-Oncology. 53: 149–160, 2001). Briefly, flat-bottom 96-well plates are coated with purified ECM proteins (collagen IV, laminin, fibronectin, vitronectin, hyaluronic acid, and tenascin) resuspended in PBS at 1, 10, or 100 µg/ml overnight at 4° C. The protein solution is removed, and the wells blocked with 1% BSA in PBS for 1 hour at room temperature. The cells are harvested from subconfluent monolayers using 0.05% trypsin-0.53 mM EDTA in Ca-free/Mg-free HBSS. Cells are resuspended in DMEM containing 5% fibronectin-free serum and plated at a density of $5 \times 10^4$ cells/50 µl into wells containing 50 µl of medium. The 96-well plates are placed on ice for 30 min followed by 1 h at 37° C. Plates are shaken on an orbital shaker for 6 min at 350 rpm. Medium and unattached cells are aspirated off. 100 µl of PBS are added to each well and the plates shaken a second time, and aspirated. Attached cells are fixed in 1% glutaraldehyde for 30 min rinsed with PBS ×3, stained with 0.1% crystal violet for 10 min, washed three times with PBS, solubilized in 1% SDS, and quantified by reading the absorbance at 540 nm on a spectrophotometer.

iv. Cell migration assays. Cell migration is quantified using the method described in Rempel, S. A., et al., J Neuro-Oncology. 53: 149–160, 2001; and Menon, P. M., et al., Int J Oncology. 17: 683–693, 2000. Briefly, Teflon-coated 10-well slides (Creative Scientific Methods, Inc.) are autoclaved and the wells coated with 45 µl of ECM at 100 µg/ml for 1 hour at 37° C. Wells are rinsed three times with Dulbecco's 1× PBS (Life Technologies, Inc.) and blocked with 45 µl of 1% BSA for 30 min at room temperature. The BSA is aspirated and 50 µl of PBS are added to each well. Slides are stored at 4° C. overnight in a 100-mm petri dish humidified with a 35-mm petri dish filled with sterile $dH_2O$ to prevent drying.

Wild-type U87 and GDOX-transfected cells growing in monolayer are harvested from T25 flasks and counted using a hemocytometer. Conditioned medium is collected from cells after 5 days of culture, and diluted 1:4 with DMEM+ 10% FBS. The harvested cells are resuspended in 25% conditioned medium at $1 \times 10^6$ cells/ml and kept on ice. The Teflon-coated slides are removed from 4° C., the PBS aspirated from the wells, and 50 µl of 25% conditioned medium are added to each well. $2 \times 10^3$ cells are seeded into the center of each well using the cell sedimentation manifolds per manufacturer's instructions. Slides are placed on ice for 1 hour, followed by 1 hour incubation at 37° C. Water-saturated filter paper strips are placed in the dish to prevent media evaporation during incubation. Manifolds are removed from the slide after 1 hour incubation, and fresh 25% conditioned medium (50 µl) is added to each well. A cover slide is mounted 1 mm above the Teflon slide using silicone suspension pads that fit on the ends of the Teflon slide. Cells are photographed for baseline radius measurements (0 h) and returned to the 37° C. incubator to allow migration to proceed.

Serial images of the circular area occupied by the attached cells in each well are taken at 0, 24, and 48 hours, using a KODAK camera attached to an Olympus 1X50 microscope and connected to a Macintosh G4 computer. Images are captured using Adobe Photoshop software, and the diameter of the cell population measured using an image analysis software program. Quantitative migration measurements are calculated as the increase in radius beyond the initial radius (0 h) of the cell population.

v. Cell invasion assays. Matrigel invasion assays are used to measure the invasiveness of parental U87 and vector-, random antisense GFAP-, sense GDOX-, and antisense GDOX-transfected U87 clones through Matrigel-coated transwell inserts (Becton Dickinson) per manufacturer's instructions. Briefly, transwell inserts with 8 µm pores are coated with a final concentration of 1 mg/ml Matrigel, and 200 µl of cell suspension ($1 \times 10^6$ cells/ml) are added in triplicate wells. After 24-hour incubation, the cells that pass through the filter into the lower wells are quantified and expressed as a percentage of the sum of the cells in the upper and lower wells. Cells on the lower side of the membrane are fixed, stained with Hema-3, and photographed as described previously (Kondraganti, S., et al., Cancer Research. 60: 6851–6855, 2000).

Three-dimensional spheroid confrontation assays can also be used to measure the invasiveness of glioma spheroids according to previously described procedures in which glioma spheroids were co-cultured with fetal rat brain aggregates (Go, Y., et al., Clin Exp Metastasis. 15: 440–446, 1997; Golembieski, W. A., et al., Int J Devl Neuroscience. 17: 463–472, 1999; Vajkoczy, P., et al., Int J Cancer. 87: 261–268, 2000). Tumor spheroids are stained with 25 µg/ml of the red fluorescent dye DiI (1,1'-dioctadecyl-3,3,3',3'-tetramethyllindo-carbocyanin perchlorate) and combined with fetal rat brain aggregates stained with 30 µg/ml of the green fluorescent DiO dye (3,3'-dioctadecyloxacarbo-cyanine perchlorate).

Confronting pairs consisting of either parental U87, vector-, random antisense GFAP-, sense GDOX-, or antisense GDOX-transfected U87 cells with fetal rat brain spheroids are made by transferring individual aggregates to microwell dishes by means of a sterile needle. At different time intervals, serial 1-µm-thick sections are obtained from the surface through the center of the co-cultures with a confocal laser-scanning microscope. DiI and DiO fluorescence emissions are detected simultaneously using an argon laser at 488 nm with FITC filter optics (522 nm) and a helium/neon laser at 543 nm with Texas Red filter optics (585 nm), respectively. The remaining volume of the brain aggregate or tumor spheroid during co-cultures at 24, 48, and 72 hours is quantitated using imaging software (Laser Sharp). The difference in invasiveness is assessed by quantitative density mapping between the images observed for the control vs. GDOX-sense and antisense clones.

vi. Apoptosis assays. The effects of GDOX under- and overexpression on apoptosis in can be assayed in control and transfected U87 human glioblastoma cell lines using a variety of methods, including:

(a) Cell morphological analysis for apoptotic cells with DAPI staining is performed using $2 \times 10^5$ parental U87, vector-, random antisense GFAP-, sense GDOX-, and antisense GDOX-transfected U87cells plated onto poly-L-lysine-coated coverslips and cultured overnight. The next day, cells are washed once with PBS and then fixed in 3.7% paraformaldehyde in PBS for 30 min at room temperature, followed by two washes of PBS. Cells are permeabilized in 1% Triton X-100 in PBS for 3 min and washed twice in PBS. Cells are stained with the nuclear staining dye DAPI (10 µg/ml in PBS; Sigma) for 20 nun at room temperature, followed by two washes in PBS. Cells on coverslips are mounted onto glass slides, and nuclear staining visualized using an Olympus fluorescent microscope (at 400× magnification). The number of cells with apoptotic bodies and total nuclei from 5 high-power fields are counted, and the percentage of apoptosis is calculated as the mean +SD.

(b) TUNEL staining for in situ DNA strand breaks is performed according to manufacturer's recommendations (APO-Direct TUNEL direct immunofluorescence kit; PharMingen). Cells are viewed with an Olympus fluorescence confocal microscope. TUNEL-positive cells are counted at ×400. The apoptotic index is calculated as a ratio of apoptotic cell number:total cell number in each field.

(c) DNA fragmentation by agarose gel electrophoresis is performed using $2 \times 10^6$ cells collected and washed once in PBS. Cell pellets are lysed in 0.5 ml of lysis buffer [10 mM Tris (pH 7.6) and 0.6% SDS], followed by the addition of 4 M NaCl to a final concentration of 1 M, and mixed well. Lysates are centrifuged at 12,000 rpm for 30 min at 4° C. Supernatants are collected and incubated at 37° C. for 60 min in the presence of 50 µg/ml RNase A, followed by a phenol:chloroform (1:1) extraction. Genomic DNA is precipitated with 2 volumes of 100% ethanol in the presence of 0.01 M $MgCl_2$ and 25 µg/ml tRNA at −80° C. for at least 2 hours. DNA is pelleted by centrifugation at 12,000 rpm for 30 min at 4° C. Pellets are washed twice with 70% ethanol and then air-dried before being resuspended and stored in 25 µl of TE [10 mM Tris and 1 mM EDTA (pH 8.0)] buffer. The amount of DNA is determined by $A_{260\ nm}$ value. Equal amounts of DNA are loaded onto a 0.8% agarose gel and electrophoresed in 0.5× TBE buffer [45 mM Tris-borate and 1 mM EDTA 9pH 8.0)] for 16 hours at 2 V/cm. DNA fragmentation is visualized by ethidium bromide (0.5 µg/ml) staining under UV light. Images are captured using the Kodak DC120 Digital Access System (Kodak) and processed using Adobe Photoshop software.

Example 12

In vivo Tumorigenicity and Survival Assays

This example describes in vivo assays that employ a xenograft model to elucidate mechanisms by which GDOX promotes tumorigenesis. These assays can also be used to test the ability of a candidate therapeutic directed against GDOX or one of its gene products to disrupt the tumorigenic effects of GDOX overexpression.

For in vivo tumorigenicity and survival studies, parental U87 and vector, sense and antisense stable transfectant cells are trypsinized and resuspended in serum-free medium. Immunodeficient BALB/c nude (nu/nu) mice (Charles River) are anesthetized. Trypsinized cells derived from each of the cell line clones are either injected subcutaneously ($1 \times 10^7$ s.c. in 100 µl serum-free medium) into the flanks or inoculated stereotactically intracranially ($5 \times 10^5$ i.c. in 10 µl serum-free medium) into the brains of 4–5 week-old female nude mice as described previously. The different groups are as follows:

| Cells injected | s.c. tumors ($1 \times 10^7$ cells) | i.c. tumors ($5 \times 10^4$ cells) |
|---|---|---|
| Serum-free media (control) | 20 | 20 |
| Parental U87 | 20 | 20 |
| U87-pBK-CMV (empty vector) | 20 | 20 |
| U87-antisense GFAP (random antisense) | 20 | 20 |
| U87-sense GDOX | 20 | 20 |
| U87-antisense GDOX | 20 | 20 |
| TOTAL: | 120 animals | 120 animals |

Ten animals in each group are used for tumorigenicity assays. The in vivo tumors are allowed to grow for 2–4 weeks (for i.c. tumors) or 6–8 weeks (for s.c. tumors). Mice injected with s.c. tumors are sacrificed at day 42 after injection, while mice with i.c. tumors are killed at day 14 post-implantation. The animals are perfusion fixed. The s.c. tumors or brains are carefully resected by surgical dissection. Each specimen is fixed in 10% formalin/PBS, embedded in paraffin, and stained with H&E according to standard protocols. Immunohistochemical analysis is performed according to standard procedures incorporating the Vectastain ABC kit (Vector Laboratories) per manufacturer's protocol, followed by incubation using 3,3'-diaminobenzidine tetrachloride as a chromophore.

Assessment of tumor cell proliferation is performed by Ki-67 and MIB-1 immunohistochemistry on formalin-fixed paraffin-embedded tissues. The Ki-67 and MIB-1 labeling indices are determined as the ratio of labeled:total nuclei in 4 high-power (×400) fields.

Necrosis is assessed by histological analysis of H&E-stained tissues using a computerized image analysis system. Digital images of 4 random sections at =200 magnification are taken, and the areas of necrosis are calculated as a percentage of the total area in each field.

Angiogenesis is assessed by immunohistochemistry using an anti-CD31 antibody (PharMingen) without counterstain and quantitated as microvessel area using a computerized image analysis system. Microvessel area is determined by capturing 4 digital images of the sections at ×200 magnification and measuring the total amount of staining in each section. This value is represented as a percentage of the total area in each field. Angiogenesis is also assessed by immunostaining for vascular endothelial growth factor (VEGF), using an anti-VEGF antibody (PharMingen).

Invasion of the tumor cells into the mouse brains is assessed by in situ hybridization with a Blur-2 human-specific DNA probe, which would identify all human cells in the background of mouse cells, using a protocol previously described (Rempel, S. A., et al., J Neuropathol Exp Neurol. 57: 1112–1121, 1998).

Ten animals in each group injected with s.c. tumors are used for tumor growth curve studies, and ten in each group implanted with i.c. tumors are evaluated for survival. Animals are inspected every other day for the appearance of visible tumors s.c. or for neurological symptoms from i.c. tumors.

For the s.c. tumors, caliper measurements are taken twice a week. Tumor volumes in $mm^3$ are determined using the formula (length×width$^2$)/2, where length is the longest diameter axis, and width the measurement at right angles to the length. At necropsy, tumors are carefully removed by surgical dissection and weighed. Data are expressed as mean tumor volume or weight±SE for each group.

For the i.c. tumor xenografts, animals in the different groups are monitored for survival. Survival estimates and mean survival times are determined using the Kaplan-Meier method and analyzed by Wilcoxon analysis.

Example 13

Transgenic Mouse Assays

This example describes in vivo assays that employ a transgenic animal model to elucidate mechanisms by which GDOX promotes tumorigenesis. These assays can also be used to test the ability of a candidate therapeutic directed against GDOX or one of its gene products to disrupt the tumorigenic effects of GDOX overexpression.

To confirm that expression of the putative GDOX oncogene is sufficient for tumor formation in vivo, transgenic technology is used to develop a mouse tumor model. GDOX transgenic mice are generated by embryonic stem (ES) cell-mediated gene transfer of GDOX under the control of the astrocyte-specific GFAP promoter, using a modification of the method described by Ding et. al. (Cancer Research. 61: 3826–3836, 2001).

Plasmid construction. The plasmid pGfa 2lac1, which contains a 2.2-kb fragment of the human GFAP promoter that directs expression the lacZ (β-galactosidase) gene, is used (Holland, E. C. and Varmus, H. E., Proc Natl Acad Sci USA. 95:1218–1223, 1998). The lacZ gene is removed by digestion with BamH1 and replaced with an insert containing the GDOX cDNA from pBK-CMV. The GFAP-GDOX fragment is inserted into the PloxP-neo vector, which contains a neomycin selection marker flanked by two identically oriented loxP sites. An IRESLacZ cassette, in which the LacZ gene is fused to a nuclear localization signal and an IRES sequence, are introduced into the vector to form the transgenic construct: GFAP-GDOX-IRESLacZpolyA-loxP-neo-loxP.

Cell culture transfection and in vivo differentiation. ES01 cells (ES Cell International), a developed stem cell line listed on the NIH Human Embryonic Stem Cell Registry, is grown per previously described protocols (Nagy, A. Production and analysis of ES-cell aggregation chimeras, p. 177–206. New York: Oxford University Press, Inc., 1999). For transfection, approximately $5 \times 10^5$ ES01 cells are mixed with 20 μg of linearized DNA and electroporated at 250 V, 500 μF, using a Gene Pulser (Bio-Rad). After selection with 200 μg/ml G418 (Life Technologies) for 7–8 days, colonies are picked and grown in 96-well plates. In vitro differentiation of ES cells to astrocytes is performed as described previously (Ding, H., et al., Cancer Research. 61: 3826–3836, 2001; Fraichard, A., et al., J Cell Sci. 108: 3181–3188, 1995).

Positive ES clones are used for aggregation with mouse embryos following described protocols. Some chimeric embryos are dissected, fixed, and stained with X-Gal. Living chimeras are tested for germ-line transmission by mating with C57B1/6 females.

Genotyping. To determine the genotype and transgene copy number in the GFAP-GDOX transgenic mice, genomic DNA is prepared from tail biopsy samples and used in PCR and Southern blot analysis.

Brain sectioning, histology, and immunohistochemistry. The animals are sacrificed, and the brains are fixed in 4% formaldehyde/0.4% glutaraldehyde/1× PBS for 36 hours and then dehydrated in 20% sucrose/2% glycerol/1× PBS. Frozen sections (40 μm) are obtained using a cryostat microtome, and stained with H&E according to standard protocols. Iumunohistochemical staining for GFAP is performed using a monoclonal anti-GFAP antibody (Boehringer) to look for evidence of glial tumor formation. Other organs in the transgenic mice can also be examined at autopsy.

If tumors are found in these transgenic animals, histological examination and immunohistochemical analysis are performed according to the standard protocols described above to assess tumor cell proliferation (using anti-Ki67 and anti-MIB-1 immunostaining), necrosis (H&E), angiogenesis (anti-CD31, anti-VEGF immunostaining), and invasion (in situ hybridization with Blur-2).

For ultrastructural analysis, tumors are post-fixed in osmium tetroxide, dehydrated, and epoxy-embedded. 30-nm sections are mounted on copper grids, stained with lead citrate and uranyl acetate and examined on an electron microscope.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting proliferation of glioblastoma cells in vitro comprising contacting a glioblastoma cell with a molecule selected from the group consisting of a GDOX antibody that specifically binds to the amino acid sequence of SEQ ID NO: 2, and the nucleic acid sequence comprising the full length antisense of SEQ ID NO: 1.

2. The method of claim 1, wherein said antisense molecule specifically hybridizes to SEQ ID NO: 1 under the following conditions:

5×SSC (wherein SSC is 0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C. with washes at 42° C. in 0.2×SSC and 50% formamide at 55° C., followed by a high-stringency wash consisting of 0.1×SSC containing ethylenediaminetetraacetic acid (EDTA) at 55° C.

3. The method of claim 1, wherein the cell is a human cell.

4. A method for treating glioblastoma in a subject comprising admimsterrng to the subject a GDOX antibody that specifically binds to the amino acid sequence of SEQ ID NO: 2.

5. A method for inhibiting proliferation of glioblastoma cells comprising contacting a glioblastoma cell with a GDOX antibody that specifically binds to the amino acid sequence of SEQ ID NO: 2.

* * * * *